United States Patent [19]

Sinclair et al.

[11] Patent Number: 5,262,533
[45] Date of Patent: Nov. 16, 1993

[54] AMINO O-ARYL MACROLIDES HAVING IMMUNOSUPPRESSIVE ACTIVITY

[75] Inventors: Peter J. Sinclair, Highland Park; Helen M. Organ, Roselle Park; Matthew J. Wyvratt, Mountainside, all of N.J.

[73] Assignee: Merck & Co., Inc., Rahway, N.J.

[21] Appl. No.: 876,634

[22] Filed: May 6, 1992

Related U.S. Application Data

[63] Continuation-in-part of Ser. No. 698,889, May 13, 1991, abandoned.

[51] Int. Cl.$^5$ .................. C07D 491/16; A61K 31/395
[52] U.S. Cl. ............................ 540/456; 514/291; 514/417
[58] Field of Search .......................................... 540/456

[56] References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 5,011,844 | 4/1991 | Fehr | 514/291 |
| 5,064,835 | 11/1991 | Bochis et al. | 514/291 |
| 5,110,811 | 5/1992 | Okuhara et al. | 514/183 |
| 5,162,334 | 11/1992 | Goulet et al. | 514/291 |

FOREIGN PATENT DOCUMENTS

| | | | |
|---|---|---|---|
| 0402931 | of 0000 | European Pat. Off. | 540/456 |
| 0463690 | of 0000 | European Pat. Off. | 540/456 |
| 2245891A | of 0000 | United Kingdom | 540/456 |
| WO92/00313 | of 0000 | World Int. Prop. O. | |
| WO92/03441 | of 0000 | World Int. Prop. O. | 540/456 |
| WO91/04025 | of 0000 | World Int. Prop. O. | 540/456 |
| WO92/05179 | of 0000 | World Int. Prop. O. | 540/456 |
| WO91/13899 | of 0000 | World Int. Prop. O. | |

OTHER PUBLICATIONS

Tanaka, et al., J. Am. Chem. Soc., 1987, 109 5031–5033.

Primary Examiner—Robert T. Bond
Attorney, Agent, or Firm—Charles M. Caruso; J. Eric Thies

[57] ABSTRACT

Amino O-aryl macrolides of the general structural Formula I:

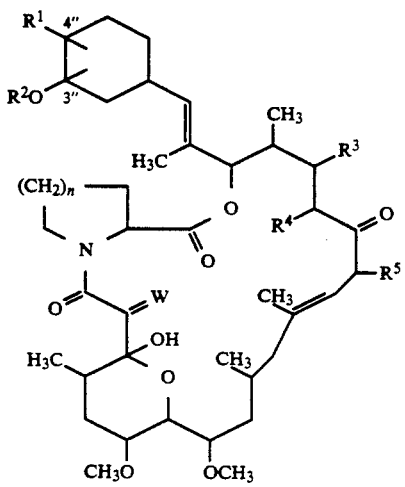

have been prepared from suitable precursors by arylation and amination at C-3"/C-4" of the cyclohexyl ring. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma; as hair revitalizing agents, especially in the treatment of male pattern alopecia or alopecia senilis; in the reversal of multidrug resistance of tumor cells; in treatment of inflammation of mucosa and blood vessels, gastric ulcers, vascular damage, ischemic bowel disease, inflammatory bowel disease, necrotizing enterocolitis, intestinal lesions associated with thermal burns; in the treatment of cytomegalovirus infection; and in the treatment of idiopathic thrombocytopenic purpura and Basedow's disease.

16 Claims, No Drawings

AMINO O-ARYL MACROLIDES HAVING IMMUNOSUPPRESSIVE ACTIVITY

This application is a continuation-in-part of copending application Ser. No. 07/698,889, filed May 13, 1991 now abandoned.

SUMMARY OF THE INVENTION

The present invention is related to amino O-aryl macrolides and derivatives which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis, and glomerulonephritis), infectious diseases and/or the prevention of rejection of foreign organ transplants, e.g. bone marrow, kidney, liver, heart, skin, small-bowel, and pancreatic-islet-cell transplants, the topical treatment of inflammatory and hyperproliferative skin diseases and cutaneous manifestations of immunologically-mediated illnesses (such as psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), reversible obstructive airways disease, particularly asthma, and/or hepatic injury associated with ischemia.

More particularly, this invention relates to compounds of the general structural Formula I:

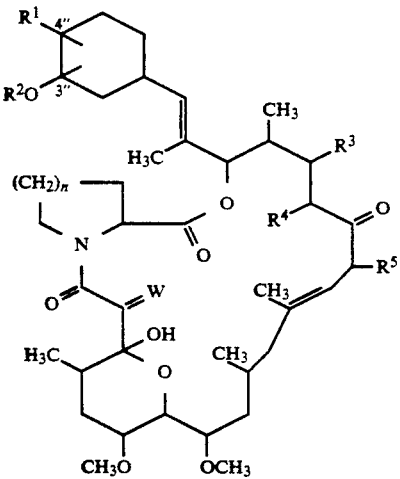

wherein $R^1$, $R^2$, $R^3$, $R^4$, $R^5$, W and n are hereinafter defined.

This invention also relates to pharmaceutical compositions containing the compounds, and to a method of use of the present compounds and other agents for the treatment and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1,14-dihydroxy-12-[2''-(4''-hydroxy-3''-methoxycyclohexyl)-1'-methylvinyl]-23,25-dimethoxy-13, 19-21,27-tetramethyl-11,28-dioxa-4-azatricyclo[22.3.1.0^{4,9}]octacos-18-ene-2,3,10,16-tetraone (FR-900506), (FK-506), (L-679,934), 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0^{4,9}]-octacos-18-ene-2,3,10,16-tetraone (FR-900520) and related compounds which are the starting materials for the preparation of the compounds described. The synthetic preparation of the aforementioned starting material (FR-900506) has recently been reported (J. Am. Chem. Soc., 1989, 111, 1157). A Sandoz European patent application (EPO Publication No. 0,356,399) discloses stereoisomers of FR-900506 and derivatives at the 17-position. Fisons European and WIPO patent (EPO Publication No. 0,323,042 and PCT Publication No. WO89/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. A Merck European patent application (EPO Publication No. 0,428,365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds.

Fujisawa United States patents (U.S. Pat. No. 4,929,611, issued May 29, 1990 and U.S. Pat. No. 4,956,352 issued Sep. 11, 1990) disclose the use of FK-506-type compounds in treating resistance to transplantation. A Sandoz European patent (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., Clincial exp. Immunol., 1990, 82, 456-461; N. Inamura, et al., Clin. Immunol. Immunopathol. 1988, 46, 82-90), recent-onset diabetes (N. Murase, et al., Diabetes, 1990, 39, 1584-86; N. Murase, et al., Lancet, 1990, 336, 373-74), posterior uveitis (H. Kawashima, Invest. Ophthalmul. Vis. Sci., 1988, 29, 1265-71), hepatic injury associated with ischemia (M. Sakr, et al., Life Sci., 1990, 47, 687-91) allergic encephalomyelitis (K, Deguchi, et al., Brain Nerve, 1990, 42, 391-97), glomerulonephritis (J. McCauley, et al., Lancet, 1990, 335, 674), systemic lupus erythematosus (K. Takabayashi, et al., Clin. Immunol. Immunopathol., 1989, 51, 110-117), multidrug resistance (M. Naito, et al., Cancer Chemother. Pharmacol., 1992, 29, 195-200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506,

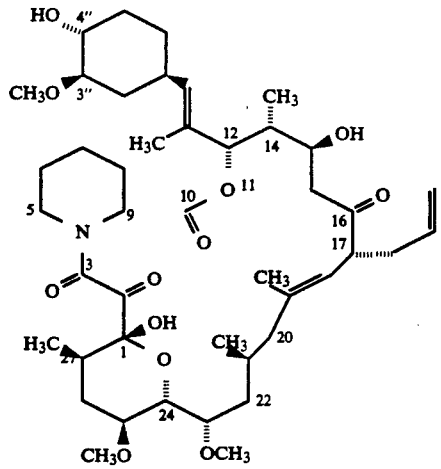

(17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. A Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al. *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117), multidrug resistance (M. Naito, et al., *Cancer Chemother. Pharmacol.*, 1992, 29, 195–200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

A. Scope of the Invention

The novel compound of this invention has structural Formula I:

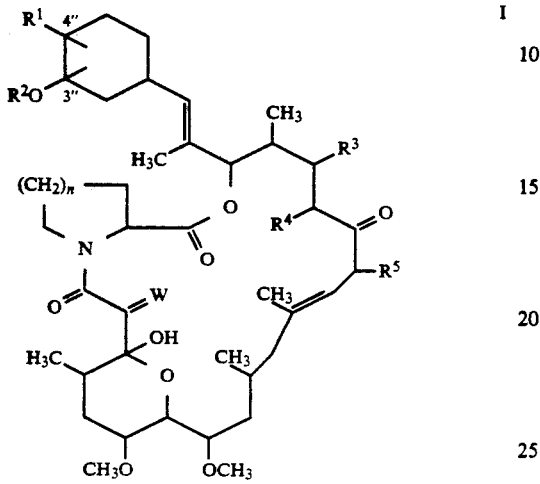

or a pharmaceutically acceptable salt thereof, wherein:
$R^1$ is selected from:
1) —$N_3$;
2) —NHCN;
3) —$NR^6R^7$, wherein $R^6$ and $R^7$ independently, are,
  a) hydrogen,
  b) $C_1$–$C_{12}$ alkyl, unsubstituted or substituted with $R^8$ and $R^9$, wherein $R^8$ and $R^9$ are independently selected from the group consisting of:
      i) hydrogen,
      ii) —OH,
      iii) $C_1$–$C_6$ alkoxy,
      iv) —O—CO—$C_1$–$C_6$ alkyl,
      v) —$NR^{10}R^{11}$, wherein $R^{10}$ and $R^{11}$ are independently, hydrogen, or $C_1$–$C_6$ alkyl, unsubstituted or substituted with phenyl
      vi) —$CONR^{10}R^{11}$,
      vii) —$CO_2H$,
      viii) —CO—O—$C_1$–$C_6$ alkyl,
      ix) —S—$C_1$–$C_6$ alkyl,
      x) —SO—$C_1$–$C_6$ alkyl,
      xi) —$SO_2$—$C_1$–$C_6$ alkyl,
      xii) halo, such as Cl, Br, F or I,
      xiii) —$C_3$–$C_7$-cycloalkyl,
      xiv) phenyl, unsubstituted or substituted with X, Y and Z,
      xv) naphthyl, unsubstituted or substituted with X, Y and Z,
      xvi) —$CF_3$,
  c) $C_3$–$C_{12}$ alkenyl, unsubstituted or substituted with $R^8$ and $R^9$, wherein $R^8$ and $R^9$ are as defined above,
  d) $C_3$–$C_7$ cycloalkyl, unsubstituted or substituted with $R^8$ and $R^9$, wherein $R^8$ and $R^9$ are as defined above,
  e) phenyl, unsubstituted or substituted with X, Y and Z,
  f) naphthyl, unsubstituted or substituted with X, Y and Z,
  g) —$SO_2$-phenyl, wherein phenyl is unsubstituted or substituted with with X, Y and Z,
  h) —$SO_2$—$C_1$–$C_6$alkyl,
  i) or where $R^6$ and $R^7$ and the N to which they are attached may form an unsubstituted or substituted 3-to 7-membered heterocyclic ring which may include one or two additional heteroatoms independently selected from the group consisting of O, S, or $NR^{10}$, wherein $R^{10}$ is as defined above, such as morpholine, thiomorpholine, piperidine, piperizine, and where the substituent(s), attached to the carbon atom(s) in the heterocyclic ring is/are independently selected from the group consisting of:
      i) hydrogen,
      ii) —OH,
      iii) $C_1$–$C_6$ alkoxy,
      iv) —O—CO—$C_1$–$C_6$ alkyl,
      v) —$NR^{10}R^{11}$, wherein $R^{10}$ and $R^{11}$ are independently, hydrogen, or $C_1$–$C_6$alkyl, unsubstituted or substituted with phenyl,
      vi) —$CONR^{10}R^{11}$,
      vii) —$CO_2H$,
      viii) —CO—O—$C_1$–$C_6$ alkyl,
      ix) —SH,
      x) halo, such as Cl, Br, F or I,
      xi) phenyl, unsubstituted or substituted with X, Y and Z,
      xii) naphthyl, unsubstituted or substituted with X, Y and Z,
      xiii) —$CF_3$;
4) —$N(R^6)CO$—O—$R^{12}$, wherein $R^6$ is as defined above and $R^{12}$ is $C_1$–$C_{12}$ alkyl, unsubstituted or substituted with $R^8$ and $R^9$, wherein $R^8$ and $R^9$ are as defined above;
5) —$N(R^6)CO$—$R^{13}$, wherein $R^6$ is as defined above and $R^{13}$ is
  a) hydrogen,
  b) $C_1$–$C_{12}$ alkyl, unsubstituted or substituted with $R^8$ and $R^9$, wherein $R^8$ and $R^9$ are as defined above,
  c) $C_3$–$C_{12}$ cycloalkyl, unsubstituted or substituted with $R^8$ and $R^9$, wherein $R^8$ and $R^9$ are as defined above,
  d) phenyl, unsubstituted or substituted with X, Y and Z,
  e) naphthyl, unsubstituted or substituted with X, Y and Z, or
  f) where $R^6$ and $R^{13}$ and the —NCO— to which they are attached may form an unsubstituted or substituted 5- to 7-membered heterocyclic ring which may include one or two additional heteroatoms independently selected from the group consisting of O, S, or $NR^{10}$, wherein $R^{10}$ is as defined above, such as pyrrolidone, or piperidinone;
6) —$N(R^{14})COCH(R^{22})NR^6R^7$ wherein $R^6$ and $R^7$ are as defined above, $R^{14}$ is selected from the definitions of $R^6$, and $R^{22}$ is
  a) hydrogen,
  b) $C_1$–$C_4$alkyl, unsubstituted or substituted with $R^{23}$ wherein $R^{23}$ is selected from the group consisting of:
      i) —OH,
      ii) $C_1$–$C_6$alkoxy,
      iii) —O—CO—$C_1$–$C_6$alkyl,
      iv) —SH, v) —S—$C_1$-$C_6$alkyl,
vi) —$NR^{10}R^{11}$, wherein $R^{10}$ and $R^{11}$ are as defined above,
vii) —$CO_2H$,
viii) —$CONH_2$,
ix) imidazolyl,
x) indolyl,
xi) phenyl, and
xii) p-hydroxyphenyl,
c) phenyl;

7) —$N(R^{14})CO(CH_2)_mNR^6R^7$, wherein m is 0 or 2-6, $R^6$ and $R^7$ are as defined above, and $R^{14}$ is selected from the definitions of $R^6$, or where $R^{14}$ and $R^6$ and the —$NCO(CH_2)_mN$— to which they are attached may form an unsubstituted or substituted 5- to 7-membered heterocyclic ring, such as 2-imidazolidone;

8) —$N=C(R^{14})$—$NR^6R^7$, wherein $R^6$ and $R^7$ are as defined above, and $R^{14}$ is selected from the definitions of $R^6$, and wherein if either $R^6$ or $R^7$ are hydrogen, the tautomeric structure —$NHC(R^{14})=NR^{6 or 7}$ is also possible;

9) —$N(R^{15})_3{}^+A^-$, wherein $R^{15}$ is $C_1$-$C_6$ alkyl, unsubstituted or substituted with phenyl or naphthyl, and wherein $A^-$ is a counterion;

10)

wherein $R^{16}$ and $R^{17}$ are independently,
a) hydrogen,
b) phenyl, unsubstituted or substituted with X, Y and Z,
c) naphthyl, unsubstituted or substituted with X, Y and Z,
d) —CN,
e) —$CF_3$,
f) —CO—$C_1$-$C_6$alkyl, or
g) —CO—O—$C_1$-$C_6$alkyl;

$R^2$ is selected from:
1) phenyl;
2) substituted phenyl in which the substituents are X, Y and Z;
3) 1- or 2-naphthyl;
4) substituted 1- or 2-naphthyl in which the substituents are X, Y and Z;
5) biphenyl;
6) substituted biphenyl in which the substituents are X, Y and Z;

$R^3$ is hydrogen, hydroxy, or $C_1$-$C_6$ alkoxy;
$R^4$ is hydrogen, or $R^3$ and $R^4$ taken together form a double bond;
$R^5$ is methyl, ethyl, propyl or allyl;
W is O or (H, OH);
X, Y and Z independently are selected from:
a) hydrogen,
b) $C_{1-7}$ alkyl,
c) $C_{2-6}$ alkenyl,
d) halo, such as Cl, Br, F or I,
e) —$(CH_2)_p$—$NR^{10}R^{11}$, wherein $R^{10}$ and $R^{11}$ are, independently, hydrogen or $C_{1-6}$ alkyl, unsubstituted or substituted with phenyl and p is 0 to 2,
f) —CN,
g) —CHO,
h) —$CF_3$,
i) —$SR^{18}$, wherein $R^{18}$ is hydrogen, $C_{1-6}$alkyl, or phenyl,
j) —$SOR^{18}$, wherein $R^{18}$ is as defined above,
k) —$SO_2R^{18}$, wherein $R^{18}$ is as defined above,
l) —$CONR^{10}R^{11}$, wherein $R^{10}$ and $R^{11}$ are as defined above,
m) $R^{19}O(CH_2)_p$— wherein $R^{19}$ is hydrogen, $C_{1-3}$ alkyl, hydroxy-$C_{2-3}$alkyl, phenyl or naphthyl and p is as defined above,
n) —$CH(OR^{20})(OR^{21})$ wherein $R^{20}$ and $R^{21}$ are $C_{1-3}$alkyl or taken together form an ethyl or propyl bridge,
o)

wherein $R^{19}$ and p are as defined above; and
p)

$$R^{19}OC(CH_2)_p-$$
$$\parallel$$
$$O$$

wherein $R^{19}$ and p are as defined above;
or any two of X, Y and Z may be joined to form a saturated ring having 5, 6 or 7 ring atoms, said ring atoms comprising 0, 1 or 2 oxygen atoms, the remaining ring atoms being carbon, such as dioxolanyl or dioxanyl; and
n is 1 or 2.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable (e.g., alkyl, aryl, $R^6$, $R^7$, $R^8$, $R^9$, etc.) occurs more than one time in any variable or in Formula I, its definition on each occurrence is independent of its definition at every other occurrence.

As used herein, the term "alkyl" includes those saturated hydrocarbon groups of a specified number of carbon atoms of either a straight, branched, or cyclic configuration. Representative examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge.

"Alkanoyl" is intended to include those alkylcarbonyl groups of specified number of carbon atoms, which are exemplified by formyl, acetyl, propanoyl and butanoyl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of either a straight- or branched-configuration and at least one unsaturation, which may occur at any point along the chain, such as ethenyl, propenyl, butenyl, pentenyl, dimethylpentyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo, and "counterion" is used to represent a small negatively-charged species, such as chloride, bromide, iodide, hydroxide, nitrate, acetate, citrate, benzoate, perchlorate, benzene sulfonate, tartrate, hemitartrate, maleate, and the like.

In the present invention it is preferred that in compounds of Formula I:

$R^1$ is selected from:
1) —$N_3$;
2) —$NR^6R^7$, wherein $R^6$ and $R^7$ independently, are,
   a) hydrogen,
   b) $C_1$-$C_{12}$ alkyl, unsubstituted or substituted with $R^8$ and $R^9$, wherein $R^8$ and $R^9$ are independently selected from the group consisting of:
      i) hydrogen,
      ii) —OH,
      iii) —O—CO—$C_1$-$C_6$alkyl,
      iv) —$NR^{10}R^{11}$, wherein $R^{10}$ and $R^{11}$ are independently, hydrogen, or $C_1$-$C_6$alkyl, unsubstituted or substituted with phenyl
      v) —$CONR^{10}R^{11}$,
      vi) —$CO_2H$,
      vii) —CO—O—$C_1$-$C_6$alkyl,
      viii) phenyl, unsubstituted or substituted with X, Y and Z,
   c) $C_3$-$C_{12}$ alkenyl, unsubstituted or substituted with $R^8$ and $R^9$, wherein $R^8$ and $R^9$ are as defined above;
3) —$N(R^6)CO$—O—$R^{12}$, wherein $R^6$ is as defined above and $R^{12}$ is $C_1$-$C_{12}$ alkyl, unsubstituted or substituted with $R^8$ and $R^9$, wherein $R^8$ and $R^9$ are as defined above;
4) —$N(R^6)CO$—$R^{13}$, wherein $R^6$ is as defined above and $R^{13}$ is
   a) hydrogen,
   b) $C_1$-$C_{12}$ alkyl, unsubstituted or substituted with $R^8$ and $R^9$, wherein $R^8$ and $R^9$ are as defined above,
   c) $C_3$-$C_{12}$ cycloalkyl, unsubstituted or substituted with $R^8$ and $R^9$, wherein $R^8$ and $R^9$ are as defined above,
   d) phenyl, unsubstituted or substituted with X, Y and Z,
5) —$N(R^{14})COCH(R^{22})NR^6R^7$ wherein $R^6$ and $R^7$ are as defined above, $R^{14}$ is selected from the definitions of $R^6$, and $R^{22}$ is
   a) hydrogen,
   b) $C_1$-$C_4$alkyl, unsubstituted or substituted with $R^{23}$ wherein $R^{23}$ is selected from the group consisting of:
      i) —OH,
      ii) $C_1$-$C_6$alkoxy,
      iii) —O—CO—$C_1$-$C_6$alkyl,
      iv) —SH,
      v) —S—$C_1$-$C_6$alkyl,
      vi) —$NR^{10}R^{11}$, wherein $R^{10}$ and $R^{11}$ are as defined above,
      vii) —$CO_2H$,
      viii) —$CONH_2$,
      ix) imidazolyl,
      x) indolyl,
      xi) phenyl, and
      xii) p-hydroxyphenyl, or
   c) phenyl;
6) —$N(R^{14})CO(CH_2)_mNR^6R^7$, wherein m is 0 or 2-6, $R^6$ and $R^7$ are as defined above, and $R^{14}$ is selected from the definitions of $R^6$, or where $R^{14}$ and $R^6$ and the —$NCO(CH_2)_mN$— to which they are attached may form an unsubstituted or substituted 5- to 7-membered heterocyclic ring, such as 2-imidazolidone;
7) —N=$C(R^{14})$—$NR^6R^7$, wherein $R^6$ and $R^7$ are as defined above, and $R^{14}$ is selected from the definitions of $R^6$, and wherein if either $R^6$ or $R^7$ are hydrogen, the tautomeric structure —$NHC(R^{14})$=$NR^{6 or 7}$ is also possible;
8) —$N(R^{15})_3^+A^-$, wherein $R^{15}$ is $C_1$-$C_6$ alkyl, unsubstituted or substituted with phenyl or naphthyl, and wherein $A^-$ is a counterion;
9)

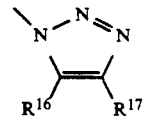

wherein $R^{16}$ and $R^{17}$ are independently,
   a) hydrogen,
   b) phenyl, unsubstituted or substituted with X, Y and Z,
   c) naphthyl, unsubstituted or substituted with X, Y and Z,
   d) —CN,
   e) —$CF_3$,
   f) —CO—$C_1$-$C_6$alkyl, or
   g) —CO—O—$C_1$-$C_6$alkyl;

$R^2$ is selected from:
1) phenyl;
2) substituted phenyl in which the substituents are X, Y and Z;
3) 1- or 2-naphthyl;
4) substituted 1- or 2-naphthyl in which the substituents are X, Y and Z;

$R^3$ is hydrogen or hydroxy;
$R^4$ is hydrogen;
$R^5$ is ethyl, propyl or allyl;
W is O or (H, OH);
X, Y and Z independently are selected from:
   a) hydrogen,
   b) $C_{1-7}$ alkyl,
   c) halo,
   d) —CN,
   e) —CHO,
   h) —$CF_3$,
   f) —$SR^{18}$, wherein $R^{18}$ is hydrogen, $C_{1-6}$alkyl, or phenyl,
   g) —$CONR^{10}R^{11}$, wherein $R^{10}$ and $R^{11}$ are as defined above,
   h) $R^{19}O(CH_2)_p$— wherein $R^{19}$ is hydrogen, $C_{1-3}$ alkyl, hydroxy-$C_{2-3}$alkyl, phenyl or naphthyl and p is 0 to 2;
   i) —$CH(OR^{20})(OR^{21})$, wherein $R^{20}$ and $R^{21}$ are $C_{1-3}$alkyl or taken together form an ethyl or propyl bridge,
   j)

$$R^{19}\overset{O}{\underset{\|}{C}}O(CH_2)_p-$$

wherein $R^{19}$ and p are as defined above; and k)

$$R^{19}O\overset{O}{\underset{\|}{C}}(CH_2)_p-$$

wherein $R^{19}$ and p are as defined above;
or any two of X, Y and Z may be joined to form a saturated ring having 5, 6 or 7 ring atoms, said ring atoms comprising 0, 1 or 2 oxygen atoms, the remaining ring atoms being carbon; and n is 1 or 2;
and pharmaceutically acceptable salts thereof.

Preferred compounds of the present invention are the compounds identified as follows:

17-allyl-1,14-dihydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-phenoxy-3"-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-dimethylamino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(4"'-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(4"'-hydroxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-acetylamino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(4"'-fluorophenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-amino-3"-(4"'-carboxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(4"'-trifluoromethylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(3"',4"'-dimethoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-1,14-dihydroxy-12-[2'-(4"-amino-3"-(4"'-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(4"'-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-amino-3"-(4"'-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(3"'-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-amino-3"-(3"'-hydroxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-N-(2-propenyl)amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone; and 17ethyl-1-hydroxy-12-[2'-(4"-acetylamino-3'-(4"'-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(2"'R-hydroxypropyl)amino-3"-phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4"-(2"'S-hydroxypropyl)amino-3"-phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4"-(2"-"R-hydroxypropyl)amino-3"-(4"'-methyl)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4"-(2"-"S-hydroxypropyl)amino-3"-(4"'-methyl)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4"-(2"'-'R-hydroxypropyl)amino-3"-(4"'-methoxy)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4"-(2"'-'S-hydroxypropyl)amino-3"-(4"'-methoxy)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4''-(2'''R-hydroxypropyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-(2'''S-hydroxypropyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-dimethylamino-3''-(3'''-methoxy)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-azido-3''-(4'''-dimethylamino)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(4'''-dimethylamino)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(4'''-methyl)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(4'''-hydroxymethyl)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(4'''-methoxy)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(3'''-methoxy)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(4'''-hydroxy)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-(4'''-formyl)phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

and pharmaceutically acceptable salts thereof.

B. Preparation of Compounds Within the Scope of the Present Invention

The starting materials for the preparation of the compounds of this invention are represented by Formula II:

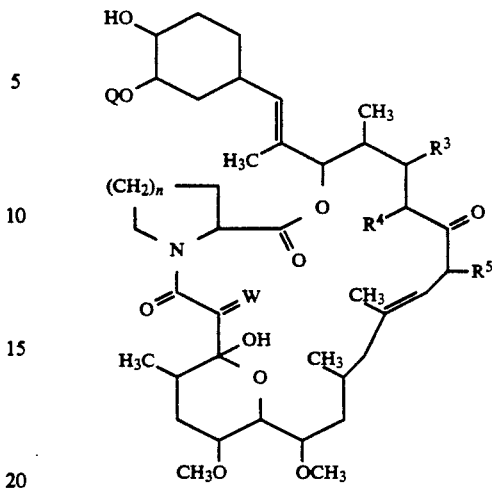

wherein:
Q is hydrogen or methyl;
W is O or (H, OH);
$R^3$ is hydrogen, hydroxy, or $C_1-C_6$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; PBJ Disclosure 63-17884; J. Am. Chem. Soc., 1987, 109, 5031; and J. Antibiotics, 1987, 40, 1249). Both biological fermentation and synthetic processes may be found. A synthetic route to compounds of Formula II can involve modifications of a route described in J. Am. Chem. Soc., 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where Q is methyl, W is O, $R^3$ is hydroxyl, $R^4$ is hydrogen, $R^5$ is allyl and n is 2; (B) where Q is methyl, W is O, $R^3$ is hydroxyl, $R^4$ is hydrogen, $R^5$ is ethyl and n is 2; (C) where Q is methyl, W is O, $R^3$ is hydroxyl, $R^4$ is hydrogen, $R^5$ is methyl and n is 2; and (D) where Q is methyl, W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4" may also be protected. In addition, the hydroxy of $R^3$ may be reduced to a hydrogen or eliminated to form a double bond with $R^4$ (by methods disclosed in U.S. Pat. No. 4,894,366 or EPO Publication No. 0,323,042). The carbonyl of W may be reduced to the alcohol by methods disclosed in EPO Publication No. 0,323,042 or by methods disclosed in U.S. Pat. No. 5,064,835.

The methyl of Q as produced may be replaced with hydrogen or demethylated and subsequently protected as desired, if necessary. This demethylation of compounds wherein Q is methyl may be carried out in a fermentation reaction using the compounds of Formula II as a feedstock. For instance, compound A named under Formula II above may be demethylated at Q above by using the microorganism Actinomycetales ATCC No. 53771 (described in U.S. Pat. No. 4,981,792, issued Jan. 1, 1991). Similarly, compound B named under Formula II above may be demethylated at Q above using the microorganism Actinoplanacete sp. ATCC No. 53771 (described in EPO Publication No. 0,349,061). In addition the compound of Formula II wherein Q is H, W is O, $R^3$ is hydroxy, $R^4$ is hydrogen, $R^5$ is ethyl and n is 2 may be produced directly by fermentation using the mutant microorganism Streptomyces hygroscopicus sup. ascomyceticus, No. 53855 (being a blocked mutant of Streptomyces hygroscopicus sup. ascomyceticus, No. 14891) (as described in EPO Publication No. 0,388,152). Similarly, the compound of Formula II wherein Q is hydrogen, W is O, $R^3$ is hydroxy, $R^4$ is hydrogen, $R^5$ is methyl and n is 2 may be produced directly by fermentation using the mutant microorganism Streptomyces hygroscopicus sup. ascomyceticus, No. 53855 (being a blocked mutant of Streptomyces hygroscopicus sup. ascomyceticus, No. 14891) (as described in EPO Publication No. 0,388,153). Also, the compound of Formula II wherein Q is hydrogen, $R^3$ is hydroxy, $R^4$ is hydrogen, $R^5$ is allyl, W is O and n is 2 and the compound of Formula II wherein the C-3" position is keto, $R^3$ is hydroxy, $R^4$ is hydrogen, R is allyl, W is O and n is 2 may be produced directly by fermentation using the microorganism Streptomyces tsukubaensis, No. 9993 (described in EPO Publication No. 0,353,678). The hydroxy of C-3" may be protected by methods similar to those known for the protection of the hydroxy's of $R^3$ and/or C-4", for example as disclosed in U.S. Pat. No. 4,894,366.

Suitable protecting groups for hydroxyl include those groups well known in the art which are: 1-(lower alkylthio) (lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyldiphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyldiphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, issued Jan. 16, 1990, and U.S. Pat. No. 4,929,611, issued May 29, 1990.

The novel processes for preparing the novel compounds of the present invention are illustrated as follows, $R^1$, $R^2$, $R^3$, $R^5$, Q, W and n are as defined above unless otherwise indicated.

REACTION SCHEME A

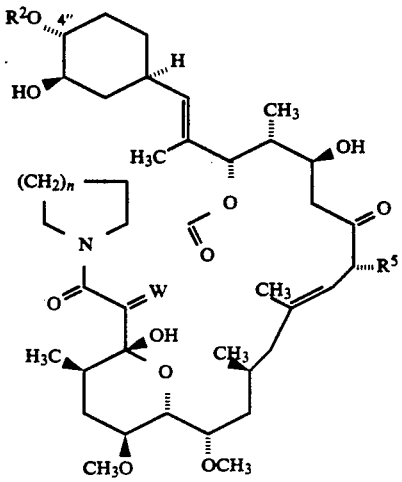

-continued
REACTION SCHEME A
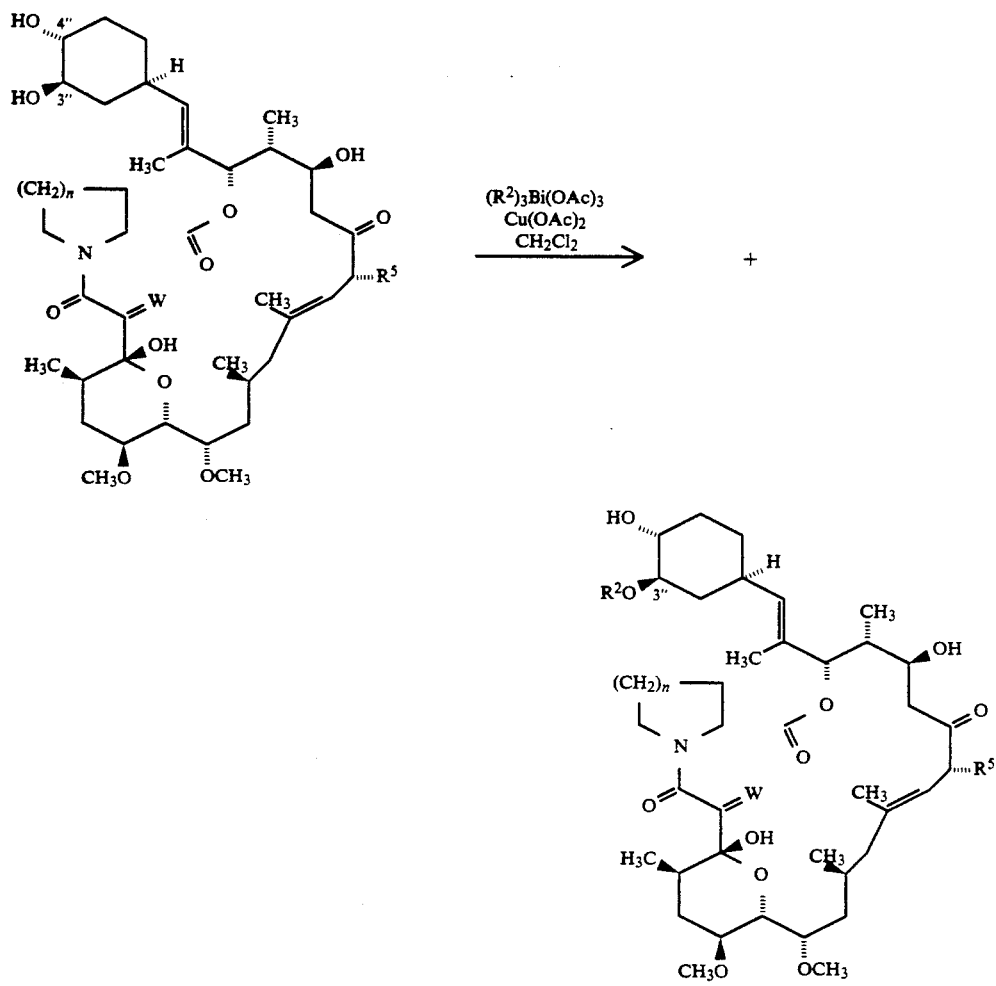
REACTION SCHEME B
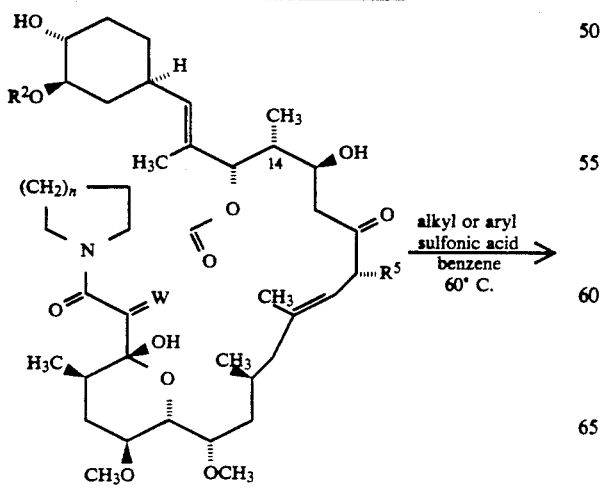
-continued
REACTION SCHEME B
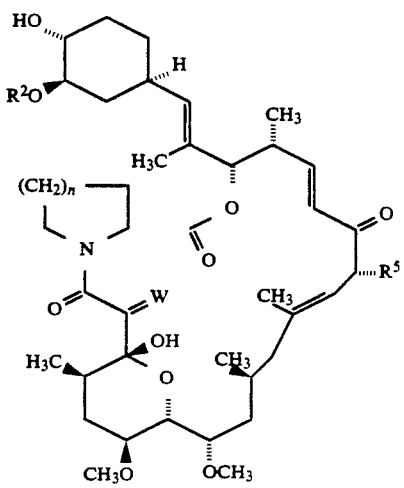

REACTION SCHEME C
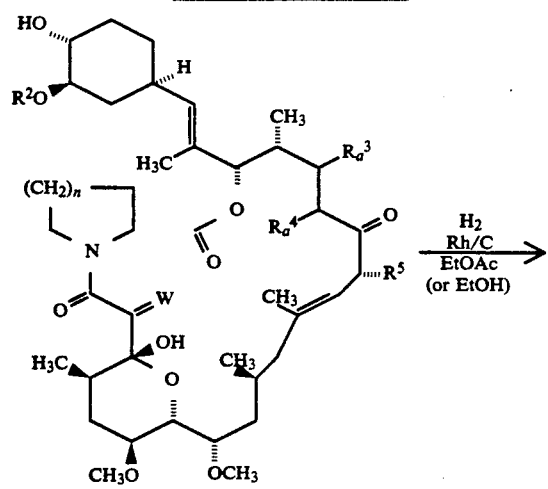
REACTION SCHEME D
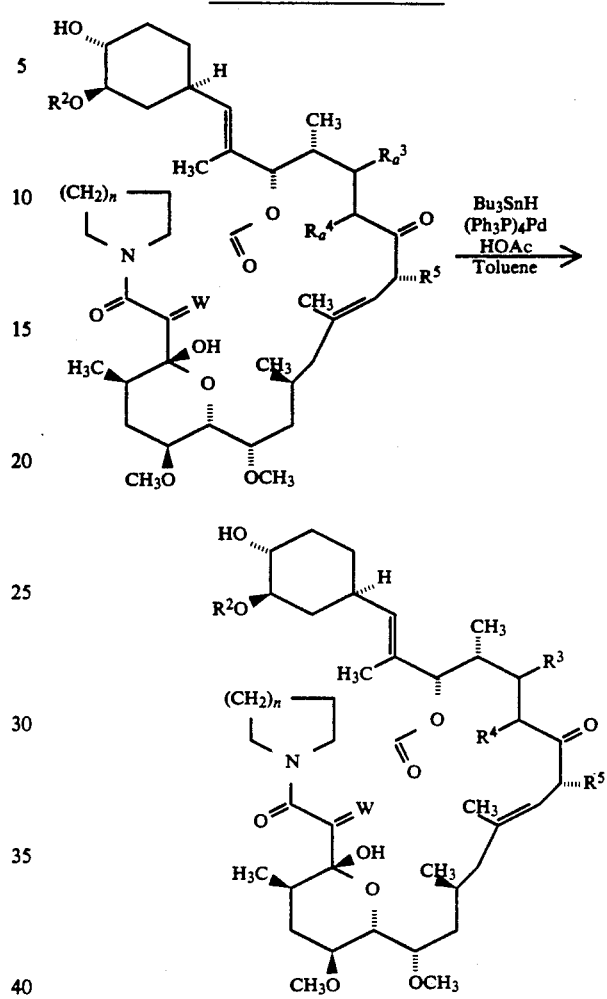
REACTION SCHEME E
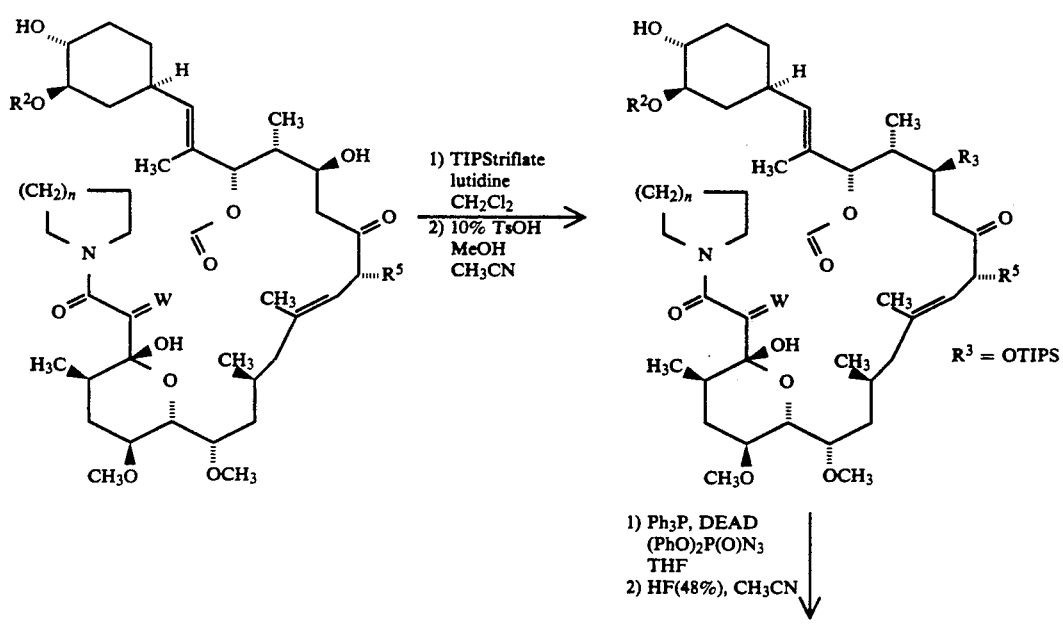

5,262,533
-continued
REACTION SCHEME E
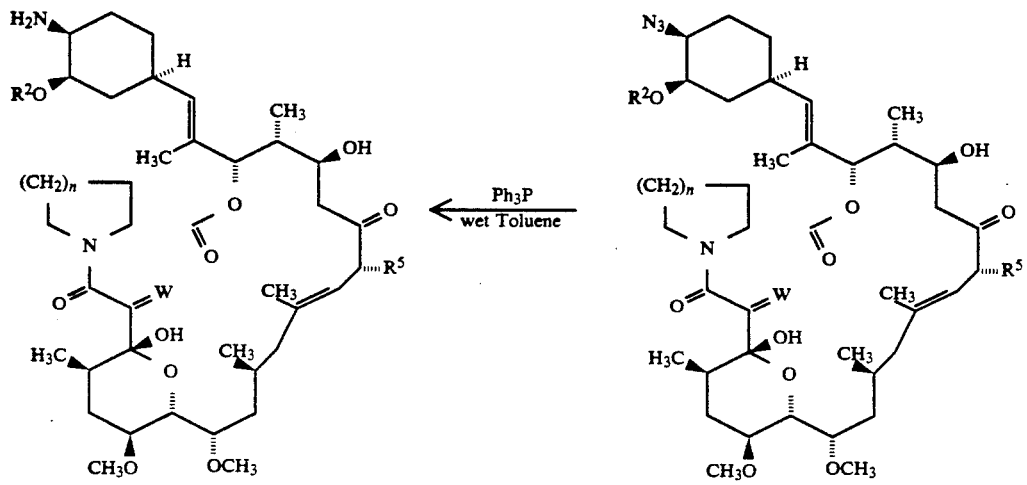
REACTION SCHEME F
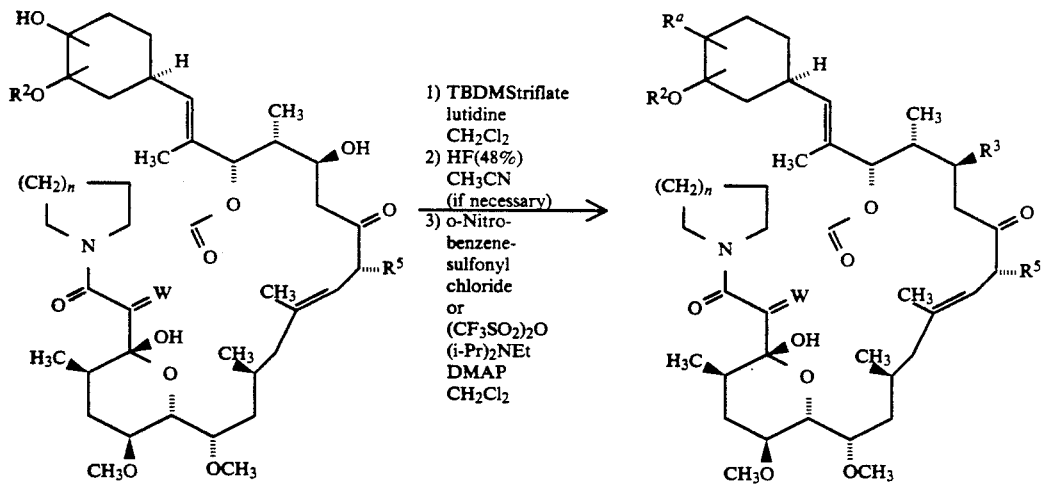
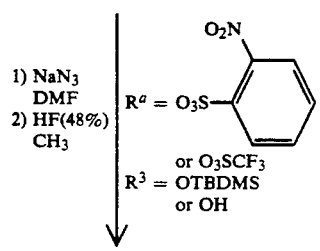

-continued
REACTION SCHEME F
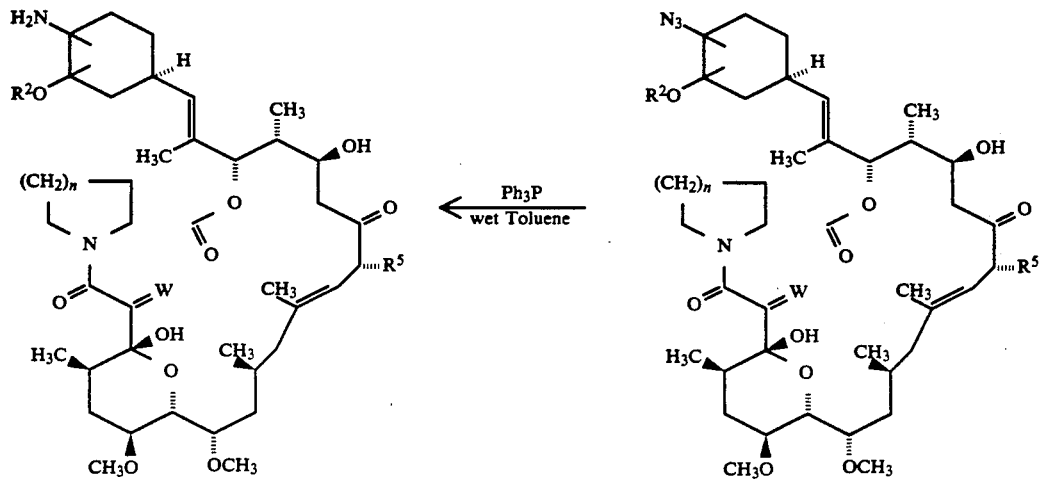
REACTION SCHEME G
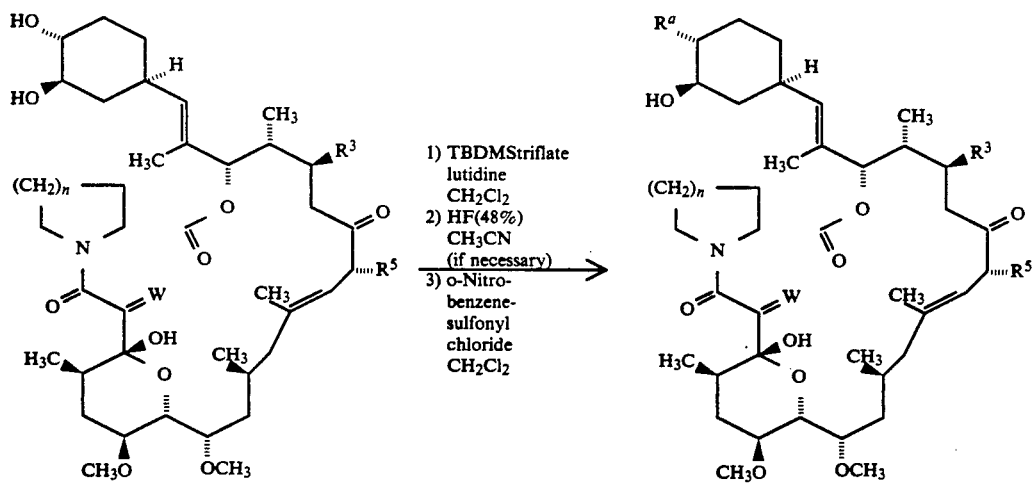
$R^3$ = OH or H
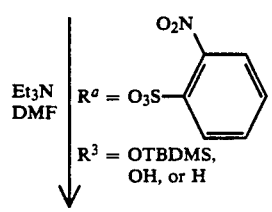

-continued
REACTION SCHEME G
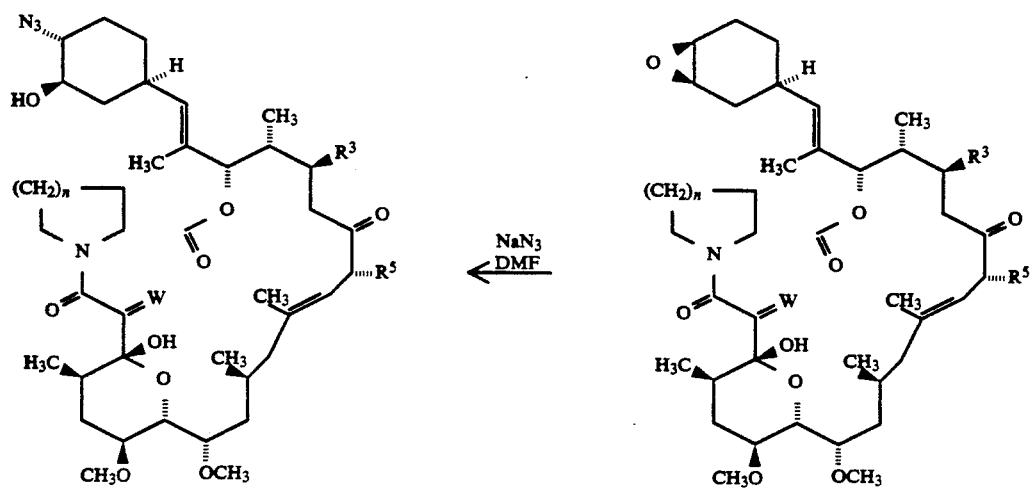
REACTION SCHEME H
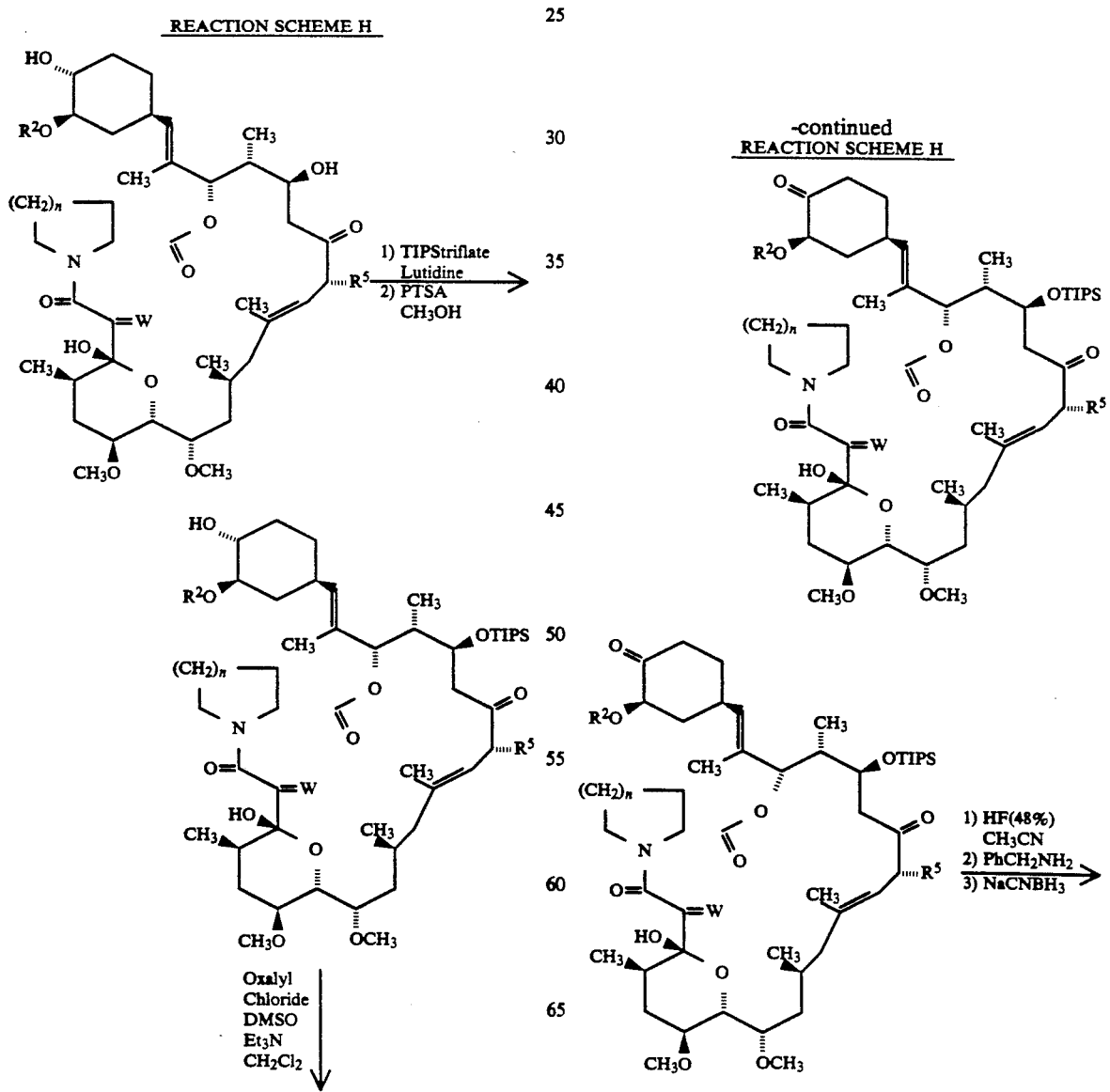

-continued
REACTION SCHEME H
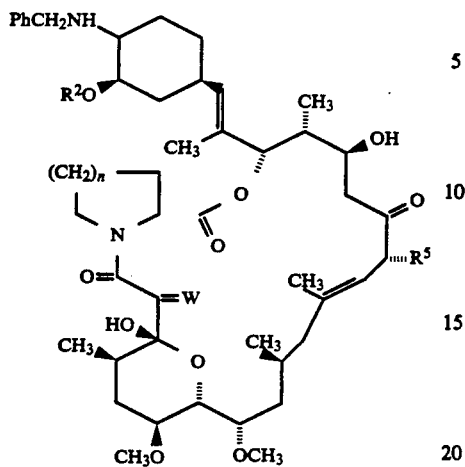
REACTION SCHEME I
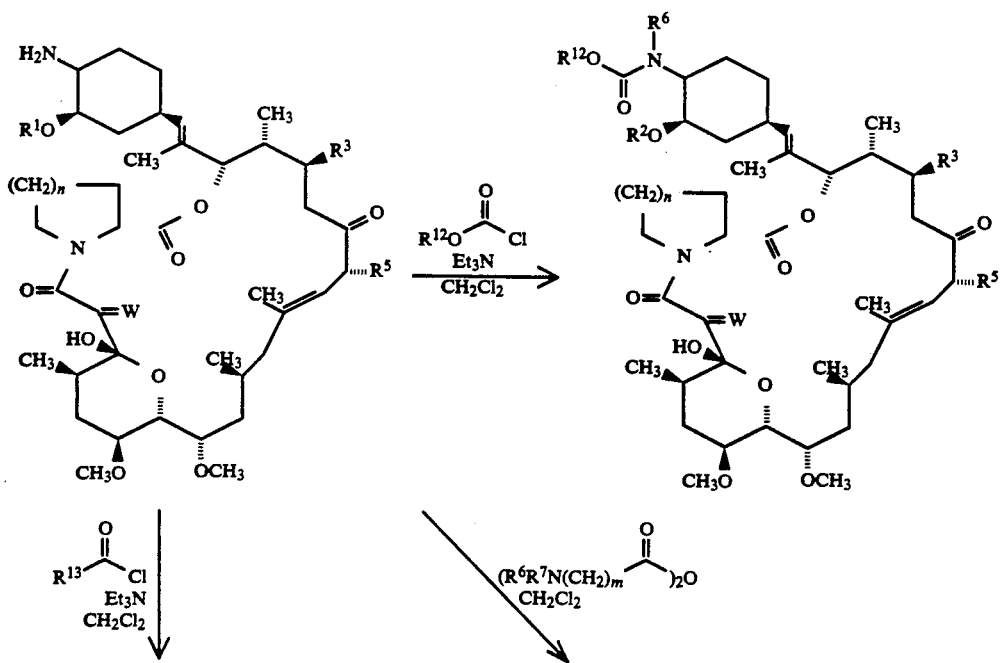

-continued
REACTION SCHEME I
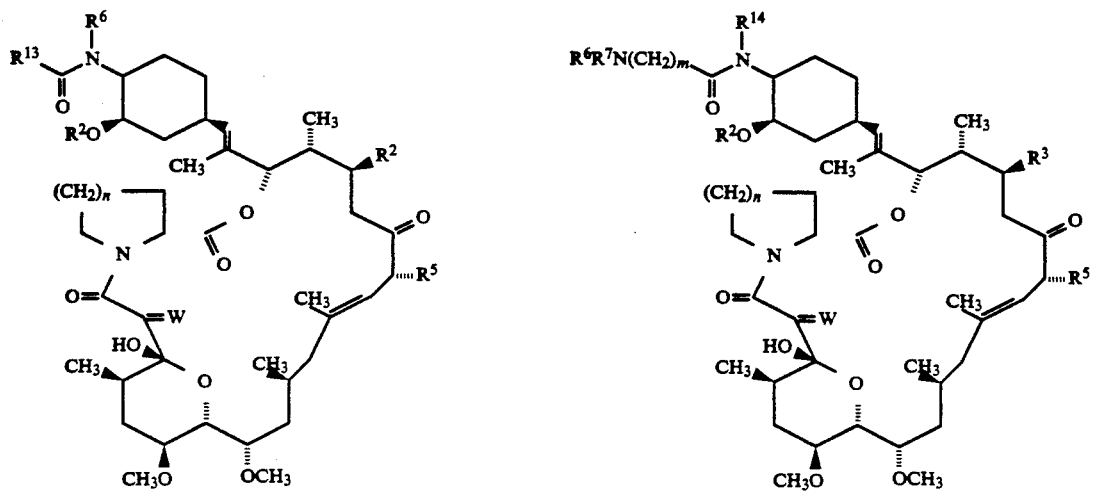
REACTION SCHEME J
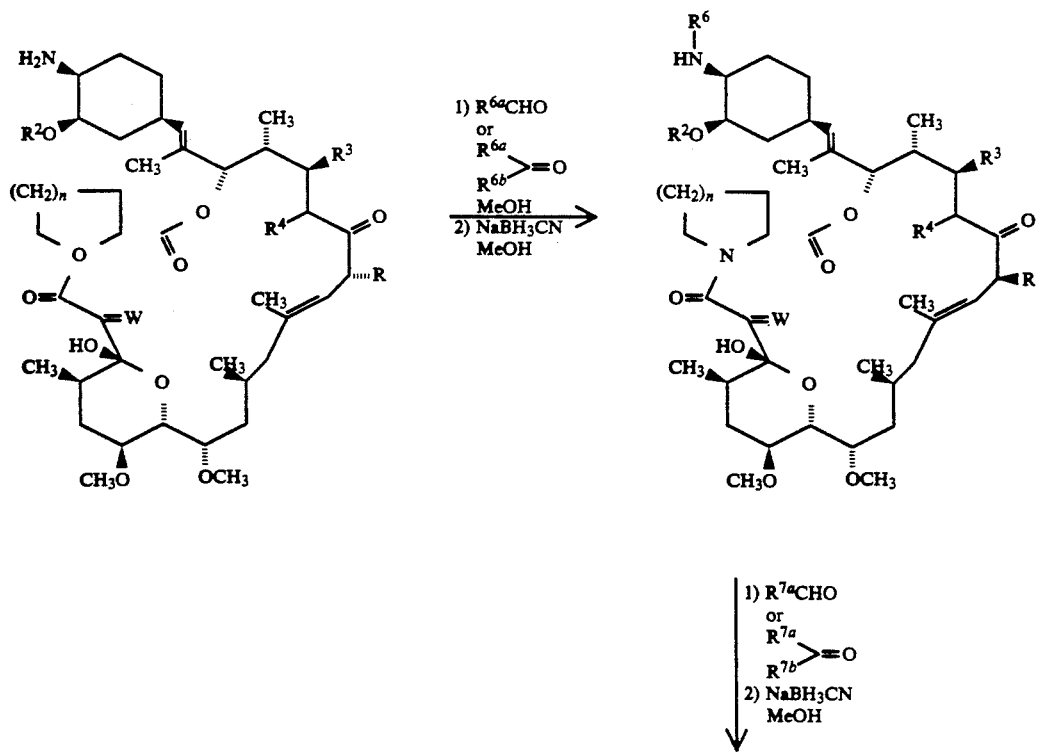

-continued
REACTION SCHEME J

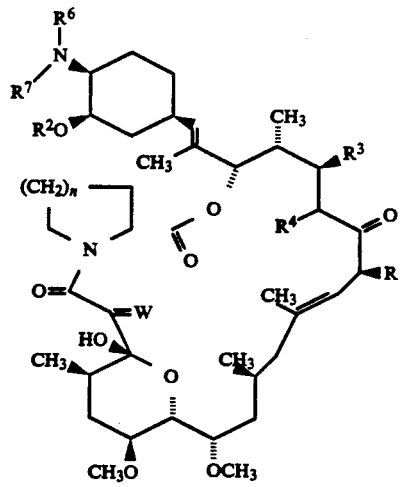

As shown in Reaction Scheme A, a solution of the 3",4"-dihydroxy macrolide in an inert organic solvent such as methylene chloride, benzene, toluene, chloroform, or the like or mixtures thereof is treated with a triarylbismuth diacetate reagent (wherein $R^2$ is aryl) (prepared immediately prior to use by the addition of acetic acid to a suspension of a triarylbismuth carbonate in an inert organic solvent such as methylene chloride, chloroform or the like or mixtures thereof) in the presence of a catalytic amount of copper(II) acetate at a temperature of 20°-50° C., preferably room temperature, for a period of one hour to seven days, preferably one day, to give a mixture of the 4"-O-aryl 3"-hydroxy macrolide and the 3"-O-aryl-4"-hydroxy macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triarylbismuth reagents may be found in Barton, D.H.E., et al., *J. Chem. Soc. Chem. Commun.*, 1986, 65 and references cited therein. The 4"-O-aryl 3"-hydroxy macrolide and the 3"-O-aryl 4"-hydroxy macrolide may be separated and purified in a conventional manner, for example, fractional crystallization, recrystallization, chromatography, and the like.

As shown in Reaction Scheme B the 14-hydroxy group of a macrolide (wherein $R^1$, $R^2$, $R^5$ and n are as defined above) may be eliminated by treatment with p-toluenesulfonic acid, benzenesulfonic acid, methanesulfonic acid, p-nitrobenzenesulfonic acid, p-bromobenzenesulfonic acid, p-chlorobenzenesulfonic acid, or p-methoxybenzenesulfonic acid, or mixtures thereof, in an inert organic solvent such as benzene, or toluene or the like at a temperature of 40° C. to solvent reflux temperature, preferably 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolide. The 14-hydroxy group may also be eliminated by activation followed by basic elimination, as described in U.S. Pat. No. 4,894,366.

As shown in Reaction Scheme C the macrolide (wherein $R^3_a$ and $R^4_a$ taken together form a double bond) is reduced under an atmosphere of hydrogen in the presence of a noble metal catalyst, such as rhodium on carbon catalyst or rhodium on alumina catalyst, at a pressure of atmospheric pressure to 40 psig, at or near room temperature in an organic solvent such as ethyl acetate or ethanol for about 1 to 24 hours, or until the requisite amount of hydrogen is absorbed to reduce the olefin and give the reduced macrolide. Alternatively, the procedures described in Reaction Scheme D may be performed.

In Reaction Scheme D the macrolide (wherein $R^3_a$ and $R^4_a$ taken together form a double bond) is reduced with tri-n-butyltin hydride in the presence of tetrakis (triphenylphosphine)palladium(O) catalyst and acetic acid in an organic solvent such as toluene or tetrahydrofuran at or near room temperature for about 2 to 10 hours to give the reduced macrolide. By changing the sequence of synthetic steps, all possible variations in substitution may be obtained. For example, the C-14 hydroxy can be eliminated and the resultant olefin reduced prior to the introduction of substituents at C-3" and/or the C-4".

Protection of the C-3" and/or the C-4" hydroxy group may be accomplished by methods known in the prior art for compounds of Formula II such as by treatment with: 2,6-lutidine and triisopropylsilyl trifluoromethane sulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like.

As shown in Reaction Scheme E the C-14-OTIPS protected macrolide is prepared from the 4",14-dihydroxy macrolide and reacted with diphenyl phosphoryl azide in the presence of triphenyl phosphine and diethyl azodicarboxylate to introduce the azide substituent at the C-4" position. The protecting group at C-14 is removed and reduction of the azide with triphenylphosphine/water gives the C-4" amino compound.

An alternate route to C-3"/C-4" amino substituted compounds is shown in Reaction Scheme F. The macrolide is protected if necessary and reacted with o-nitrobenzenesulfonyl chloride or trifluoromethanesulfonyl anhydride in the presence of an amine base to give the mono- C-3"/C-4" o-nitrobenzenesulfonyl or trifluoromethanesulfonyl derivative. The activated leaving group group is displaced by treatment with sodium azide (or an alternative nucleophillic amine), the protecting group is removed, if necessary, by treatment with hydrogen fluoride and, if necessary, the azide is reduced with triphenyl phosphine/water to give the amino compound. Azides can be reduced with other reagents known in the art, such as with hydrogen sulfide, propane-1,3-dithol, or thioacetic acid or by catalytic hydrogenation over a suitable catalyst.

As shown in Reaction Scheme G, the opposite stereochemistry of the resultant amino compound can be obtained by proceeding thru an epoxide as a synthetic intermediate. Reaction of the C-3"-beta, C-4"-alpha dihydroxy macrolide (wherein $R^3$ is hydrogen or protected hydroxy) with o-nitrobenzenesulfonyl chloride followed by separation of the isomers and treatment with a tertiary amine base, such as triethylamine, gives the two possible epoxides. The beta-epoxide may be opened by treatment with azide to give the C-3"-beta hydroxy C-4"-alpha-azido macrolide. The C-3"-hydroxyl group may be arylated, prior to reduction of the azide to the amine (by the methods of Reaction Scheme E), and the resultant amine may be further modified by methods described in Reaction Scheme I.

An amino substituent may also be introduced at C-4" by reductive amination of a keto-substituted macrolide as shown in Reaction Scheme H. The ketone at C-4" is prepared by Swern oxidation of a suitably protected hydroxy-macrolide. Reductive amination of the ketone with an appropriate amine gives the corresponding amino-macrolide as a mixture of epimers at C-4".

Compounds bearing a C-4" amino substituent may be further modified by methods which are known in the art as exemplified in Reaction Scheme I. These method include, but are not limited to such methods as: acylation with an appropriate acid halide or acid anhydride in the presence of an amine base to give the corresponding amide, coupling with an appropriate carboxylic acid to give the corresponding amide, reaction with an isocyanate to give the urea derivative, treatment with an ethyl chloroformate equivalent to give the corresponding urethane or alkylation with an appropriate alkyl halide to give the corresponding secondary, tertiary or quarternary alkyl amine.

An amino substituent may also be modified at C-3" and/or C-4" by reductive amination of an amino-substituted macrolide as shown in Reaction Scheme J (wherein $R^{6a}$ or $R^{6b}$ and $R^{7a}$ or $R^{7b}$ are respectively equivalent to $R^6$ and $R^7$ absent one methyl group). The imine is prepared by reaction of the amine with an appropriate aldehyde or ketone. Reduction of the imine with sodium cyanoborohydride or similar reducing agent gives the corresponding amino-macrolide. The reductive amination may be repeated to give mixed-disubstituted amino macrolides.

The procedures described in Reaction Schemes E-J may optionally be conducted prior to the procedures of Reaction Schemes A-D. Additionally, the procedures described in Reaction Schemes B and C may be conducted subsequent to the procedures of Reaction Schemes E-J. In general, however, it is preferred that the O-aryl group be introduced prior to the introduction of the amino functionality.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (see for example, J. Am. Chem. Soc. 1989, 111, 1157; J. Am. Chem. Soc. 1990, 112, 2998; J. Org. Chem. 1990, 55, 2786; J. Am. Chem. Soc. 1990, 112, 5583. Tetrahedron Lett. 1988, 29, 277; Tetrahedron Lett. 1988, 29, 281; Tetrahedron Lett. 1988, 29, 3895; J. Org. Chem. 1988, 53, 4643; Tetrahedron Lett. 1988, 29, 4245; Tetrahedron Lett. 1988, 29, 4481; J. Org. Chem. 1989, 54, 9; J. Org. Chem. 1989, 54, 11; J. Org. Chem. 1989, 54, 12; J. Org. Chem. 1989, 54, 15; J. Org. Chem. 1989, 54, 17; Tetrahedron Lett. 1989, 30, 919; Tetrahedron Lett. 1989, 30, 1037; J. Org. Chem. 1989, 54, 2785; J. Org. Chem. 1989, 54, 4267; Tetrahedron Lett. 1989, 30, 5235; Tetrahedron Lett. 1989, 30, 6611; Tetrahedron Lett. 1989, 30, 6963; Synlett 1990, 38; J. Org. Chem. 1990, 55, 2284; J. Org. Chem. 1990, 55, 2771; J. Org. Chem. 1990, 55, 2776; Tetrahedron Lett. 1990, 31, 1439; Tetrahedron Lett. 1990, 31, 1443; Tetrahedron Lett. 1990, 31, 3007; Tetrahedron Lett. 1990, 31, 3283, 3287).

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, toluenesulfonate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms.

The compounds of Formula I are also useful for treating or preventing inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, acne, cutaneous eosinophilias or Alopecia areata. More particularly, the compounds of Formula I are useful in hair revitalizing, such as in the treatment or prevention of male pattern alopecia or alopecia senilis, by providing epilation prevention, hair germination, and/or a promotion of hair generation and hair growth.

The compounds of Formula I are further useful for treating or preventing reversible obstructive airways disease, including conditions such as asthma, including bronchial asthma, allergic asthma, intrinsic asthma, extrinsic asthma and dust asthma, particularly chronic or inveterate asthma (for example late asthma and airway hyper-responsiveness), bronchitis and the like. The compounds of Formula I may also be useful for treating hepatic injury associated with ischemia.

The compounds of Formula I are also useful for treating multidrug resistance of tumor cells, (i.e. enhancing the activity and/or sensitivity of chemotherapeutic agents), preventing or treating inflammation of mucosa or blood vessels, $LTB_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis, or intestinal lesions associated with thermal burns, cytomegalovirus infection, particularly HCMV infection, idiopathic thrombocytopenic purpura and Basedow's disease.

Further, the compounds of Formula I are also useful for treating or preventing renal diseases selected from interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases selected from hyperthyroidism; hematic diseases selected from pure red cell aplasia, aplastic anemia, hypoplastic anemia, autoimmune hemolytic anemia, agranulocytosis and anerythroplasia; bone diseases such as osteoporosis; respiratory diseases selected from sarcoidosis, fibroid lung and idiopathic interstitial pneumonia; eye diseases selected from herpetic keratitis, conical cornea, dystrophia epithelialis corneae, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitis syndrome, polyarteritis nodosa and myocardosis; collagen diseases selected from scleroderma, Wegener's granuloma and Sjorgren's syndrome; adiposis; eosinophilic fasciitis; periodontal disease; and muscular dystrophy.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17-22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 g per patient per day, assuming a 70 kg patient). In addition, the compounds of the present invention may be administered on an intermittent basis; i.e. at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitation on the scope or spirit of the instant invention.

EXAMPLE 1

General procedure for the preparation of triarylbismuthines

To a stirred suspension of magnesium (486 mg, 20 mmol) in dry tetrahydrofuran (10 mL) is added slowly a solution of aryl halide (20 mmol) in dry tetrahydrofuran (10 mL). If necessary the mixture is warmed gently to effect grignard formation. To the stirred solution of the grignard reagent is added a solution of bismuth trichloride (1.9 g, 6 mmol) dissolved in dry tetrahydrofuran (20 mL). The resulting mixture is stirred for 24 hours. The reaction mixture is poured into a separatory funnel containing brine and extracted 4× with $CH_2Cl_2$. The organic extracts were combined and dried over anhydrous $Na_2SO_4$. The mixture was filtered and concentrated in vacuo. The triarylbismuthine is isolated and purified by flash column chromatography on silica gel.

EXAMPLE 2

A. 17-Ethyl-1,14-dihydroxy-12-[2'-(3"-phenyloxy-4"-hydroxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4"-phenyloxy-3"-hydroxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (500 mg, 0.644 mmol, 1 eq) and Cu-(OAc)$_2$ (12 mg, 0.064 mmol, 0.1 eq) in $CH_2Cl_2$ (10 ml) in a 25 ml recovery flask equipped with a magnetic stir-bar was added triphenyl bismuth diacetate [prepared immediately prior to use by addition of acetic acid (0.220 ml, 3.860 mmol, 6 eq) to a suspension of triphenyl bismuth carbonate (483 mg., 0.965 mmol, 1.5 eq) in $CH_2Cl_2$ (10 ml)]. The reaction flask was capped and the mixture stirred at room temperature for 6 hours. The flask was then fitted with a condenser and the mixture was warmed to 40° C. After 40 hours the reaction mixture was cooled, diluted with saturated aqueous $NaHCO_3$ and extracted 4 times with $CH_2Cl_2$. The organic extracts were combined, dried over anhydrous $Na_2SO_4$, filtered and concentrated in vacuo. The products were separated and purified by flash column chromatography on silica gel [eluted with 4:1 hexanes/acetone followed by preparative TLC on silica gel (eluted with 2:1 hexanes/acetone] yielding 94 mg ethyl-1,14-dihydroxy-12-[2'-(4"-phenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 110 mg 17-ethyl-1,14-dihydroxy-12-[2'-(3"-phenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR and mass spectral analysis were consistent with the desired structure).

EXAMPLE 3

A. 17-Ethyl-1,14-dihydroxy-12-[2'-(3"-(4"'-methylphenyloxy)-4"-hydroxycyclohexyl)-1'-methylvinyl]-23,25-di-methoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4"-(4"'-methylphenyloxy)-3"-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, 0.257 mmol, 1 eq) and Cu-(OAc)$_2$ (10 mg, 0.055 mmol, 0.2 eq) in $CH_2Cl_2$ (2 ml) in a round bottom flask equipped with a magnetic stir-bar was added tri(4-tolyl)bismuth diacetate [prepared immediately prior to use by addition of acetic acid (0.075 ml, 1.31 mmol, 5.1 eq) to a suspension of tri(4-tolyl) bismuth carbonate (300 mg, 0.553 mmol, 2.1 eq) in $CH_2Cl_2$ (2 ml)]. The reaction flask was fitted with a reflux condenser and the mixture warmed to 40° C. for 5 hours then stirred without heating. After 18 hours the reaction mixture was diluted with saturated aqueous $NaHCO_3$ and extracted times with $CH_2Cl_2$. The organic extracts were combined, dried over anhydrous $Na_2SO_4$, filtered and concentrated in vacuo. The products were separated and purified by preparative TLC on silica gel (eluted with 2:1 hexanes/acetone) affording 31 mg 17-ethyl-1,14-dihydroxy-12-[2'-(3"-(4"'-methylphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 42 mg 17-ethyl-1,14-dihydroxy-12-[2'-(4"-(4"'-methylphenyloxy)-3"-hydroxycyclohexyl)-1'-methylvinyl]-23,25-dimethoxy-13,19,21,27-tetramethyl-11,28- dioxa-4-azatricyclo[22.3.1.0^4,9]octacos-18-ene-2,3,10,16-tetraone. (^1H NMR and ^13C NMR analysis were consistent with the desired structure).

EXAMPLE 4

A. 17-Ethyl-1,14-dihydroxy-12-[2'-(4"-(4"'-phenoxyphenyloxy)-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone and B. 17-Ethyl-1,14-dihydroxy-12-[2'-(3"-(4"'-phenoxyphenyloxy)-4"-hydroxycyclohexyl)-1'-methylvinyl]-23,25-dimethoxy-13,19,21,27-tetramethyl-11,28-dioxa-4-azatricyclo[22.3.1.0^4,9]-octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (150 mg, 0.19 mmol, 1 eq) and Cu-(OAc)$_2$ (7 mg, 0.039 mmol, 0.21 eq) in CH$_2$Cl$_2$ (2 mL) in a round bottom flask equipped with a magnetic stir-bar was added tri(4-phenoxyphenyl)bismuth diacetate [prepared immediately prior to use by addition of acetic acid (0.070 ml, 1.22 mmol, 6.4 eq) to a suspension of tri(4-phenoxyphenyl) bismuth carbonate (230 mg, 0.30 mmol, 1.58 eq) in CH$_2$Cl$_2$ (2 mL)]. The reaction flask was fitted with a reflux condenser and the mixture warmed to 40° C. After 4 hours the mixture was cooled, diluted with saturated aqueous NaHCO$_3$, and extracted 2 times with CH$_2$Cl$_2$ the extracts were combined, dried over Na$_2$SO$_4$, filtered, and concentrated in vacuo. The products were separated and purified 3× by preparative TLC on silica gel (eluted with 3:2 hexanes/acetone) affording 35 mg 17-ethyl-1,14-dihydroxy-12-[2'-(4"-(4"'-phenoxyphenyloxy)-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone and 42 mg 17-ethyl-1,14-dihydroxy-12-[2'-(3"-(4"'-phenoxyphenyloxy)-4"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone. (^1H NMR, ^13C NMR, and mass spectral analysis were consistent with the desired structures).

EXAMPLE 5

A. 17-Ethyl-1,14-dihydroxy-12-[2'-(3"-(naphth-1-yloxy)-4"-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone and B. 17-Ethyl-1,14-dihydroxy-12-[2'-(4"-(naphth-1-yloxy)-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (250 mg, 0.32 mmol, 1 eq) and Cu-(OAc)$_2$ (15 mg, 0.08 mmol, 0.25 eq) in CH$_2$Cl$_2$ (5 ml) in a round bottom flask equipped with a magnetic stir/bar was added tri(1-naphthyl) bismuth diacetate [prepared immediately prior to use by addition of acetic acid (0.100 ml, 1.75 mmol, 5.46 eq) to a suspension of tri(1-naphthyl) bismuth carbonate (350 mg, 0.54 mmol, 1.69 eq) in CH$_2$Cl$_2$ (5 ml)]. The reaction flask was fitted with a reflux condensor and the mixture warmed to 40° C. for 5 hours then stirred at room temperature. After 16 hours the mixture was diluted with saturated aqueous NaHCO$_3$ and extracted 2 times with CH$_2$Cl$_2$. The extracts were combined, dried over anhydrous Na$_2$SO$_4$, filtered, and concentrated in vacuo. The products were separated and purified by preparative TLC on silica gel (eluted with 3:1 hexanes/acetone) yielding 49 mg 17-ethyl-1,14-dihydroxy-12-[2'-(3"-(naphth-1-yloxy)-4"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone and 39 mg 17-ethyl-1,14-dihydroxy-12-[2'-(4"-(naphth-1-yloxy)-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone. (^1H NMR analysis were consistent with the desired structures).

EXAMPLE 6

A. 17-Ethyl-1,14-dihydroxy-12-[2'-(4"-(naphth-2-yloxy)-3"-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone and B. 17-Ethyl-1,14-dihydroxy-12-[2'-(3"-(napth-2-yloxy)-4"-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (250 mg, 0.32 mmol, 1 eq) and Cu-(OAc)$_2$ (10 mg, 0.055 mmol, 0.17 eq) in CH$_2$Cl$_2$ (5.5 ml) in a round bottom flask equipped with a magnetic stir-bar was added tri(2-naphthyl) bismuth diacetate [prepared immediately prior to use by addition of acetic acid (0.100 mL, 1.75 mmol, 5.46 eq) to a suspension of tri(2-naphthyl) bismuth carbonate (350 mg, 0.538 mmol, 1.7 eq) in CH$_2$Cl$_2$ (5.5 ml)]. The reaction flask was fitted with a reflux condenser and the mixture warmed to 40° C. for 4 hours then stirred at room temperature. After 3 days the reaction mixture was diluted with saturated aqueous NaHCO$_3$ and extracted 3 times with CH$_2$Cl$_2$. The extracts were combined, dried over anhydrous Na$_2$SO$_4$, filtered, and concentrated in vacuo. The products were separated and purified by preparative TLC on silica gel (eluted with 3:1 hexanes/acetone) to give 63 mg of 17-ethyl-1,14-dihydroxy-12-[2'-(3"-(napth-2-yloxy)-4"-hydroxycyclohexyl)-1'-methylvinyl]-23,25-dimethoxy-13,19, 21,27-tetramethyl-11,28-dioxa-4-azatricyclo[22.3.1.0^4,9]octacos-18-ene-2,3,10,16-tetraone and 49 mg of 17-ethyl-1,14-dihydroxy-12-[2'-(4'-(naphth-2-yloxy)-3"-hydroxycyclohexyl)-1'-methylvinyl]-23,25-dimethoxy-13,19,21,27-tetramethyl-11,28-dioxa-4-azatricyclo[22.3.1.0^4,9]-octacos-18-ene-2,3,10,16-tetraone. (^1H NMR were consistent with the desired structures).

EXAMPLE 7

Tri(6-Methoxy-2-naphthyl)bismuth diacetate

To a stirred solution of tri(6-methoxynaphth-2-yl)bismuthine (100 mg, 0.158 mmol) in CH$_2$Cl$_2$ (8 mL) was added iodobenzene diacetate (200 mg, 0.621 mmol). The CH$_2$Cl$_2$ was removed in vacuo and the residue was dissolved in several milliliters of 4:1 hexanes/acetone plus small amount of CH$_2$Cl$_2$. The solution was passed through a silica gel plug and eluted with 4:1 hexanes/acetone. The filtrate was concentrated in vacuo. The residue was dissolved in 4:1 hexanes/acetone plus small amount of CH$_2$Cl$_2$ and passed through a second silica gel plug and eluted with 4:1 hexanes/acetone. The filtrate was concentrated in vacuo leaving 52 mg yellow residue that was used without further purification.

EXAMPLE 8

A. 17-Ethyl-1,14-dihydroxy-12-[2'-(3''-(6'''-methoxynaphth-2-yloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4''-(6'''-methoxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri-(6-methoxy-2-naphthyl) bismuth diacetate (22 mg, 0.028 mmol, 1 eq) in methylene chloride (2 ml) in a 10 mL round bottom flask equipped with a stir bar was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (22 mg, 0.028 mmol, 1 eq). To the reaction mixture was added a catalytic amount of Cu(OAc)$_2$ (approximately 20 mg). The reaction flask was fitted with a reflux condenser and the mixture was warmed to 40° C. After 1 hour the mixture was cooled, diluted with saturated aqueous NaHCO$_3$ and extracted 4 times with CH$_2$Cl$_2$. The organic extracts were combined, dried over anhydrous Na$_2$SO$_4$, filtered and concentrated in vacuo. The product was isolated by preparative thin layer chromatography on silica gel (eluted with 2:1 hexanes/acetone) giving 7.1 mg 17-ethyl-1,14-dihydroxy-12-[2'-(4''-(6'''-methoxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.35) and 9 mg 17-ethyl-1,14-dihydroxy-12-[2'-(3''-(6'''-methoxy-naphth-2-yloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.28). ($^1$H NMR and mass spectral analysis were consistent with the desired structures).

EXAMPLE 9

17-Ethyl-1,14-dihydroxy-12-[2'-(3''-(4'''-fluorophenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3'',4''-dihydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol, 1 eq) and Cu(OAc)$_2$ (3 mg, 0.0165 mmol, 0.13 eq) in CH$_2$Cl$_2$ (1 ml) in a 4 mL screw-cap vial equipped with a magnetic stir-bar is added tri(4-fluoro) bismuth diacetate [prepared immediately prior to use by addition of acetic acid (0.030 mL, 0.504 mmol, 4 eq) to a suspension of tri(4-fluorophenyl) bismuth carbonate (100 mg, 0.181 mmol, 1.4 eq) in CH$_2$Cl$_2$ (1 mL)]. The reaction vessel is capped and the mixture stirred for sufficiency time. The reaction mixture is diluted with several milliliters of saturated aqueous NaHCO$_3$ and extracted 2 times with CH$_2$Cl$_2$. The organic extracts are combined, dried over anhydrous Na$_2$SO$_4$, filtered and concentrated in vacuo. The product is isolated by preparative TLC on silica gel to afford 17-ethyl-1,14-dihydroxy-12-[2'-(3''-(4'''-fluorophenyloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 10

17-Ethyl-1,14-dihydroxy-12-[2'-(4''-(3'''-chlorophenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3'',4''-dihydroxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.189 mmol, 1 eq) and Cu(OAc)$_2$ (6.1 mg, 0.033 mmol, 0.17 eq) in CH$_2$Cl$_2$ (2.5 ml) in a round bottom flask equipped with a magnetic stirbar is added tri(4-chlorophenyl) bismuth diacetate [prepared immediately prior to use by addition of acetic acid (0.075 ml, 1.3 mmol, 6.9 eq) to a suspension of tri(4-chlorophenyl) bismuth carbonate (200 mg, 0.331 mmol, 1.75 eq) in CH$_2$Cl$_2$ (2.5 ml)]. The reaction flask is then fitted with a reflux condensor and the mixture warmed to 40° C. After sufficient time the reaction mixture is cooled, diluted with saturated aqueous NaHCO$_3$ (10 mL) and extracted times with CH$_2$Cl$_2$. The organic extracts were dried over anhydrous Na$_2$SO$_4$, filtered and concentrated in vacuo. The product is separated and purified by preparative TLC on silica gel to give 17-ethyl-1,14-dihydroxy-12-[2'-(3''-(4'''-chlorophenyloxy)-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

EXAMPLE 11

17-Ethyl-1,14-dihydroxy-12-[2'-(3''-(3''',4'''-dimethylphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(3,4-dimethylphenyl)bismuthine (200 mg, 0.381 mmol) in CH$_2$Cl$_2$ (3 mL.) is added bis(trifluoroacetoxy)iodobenzene (165 mg, 0.383 mmol). One mL of this solution was transferred to a 10 mL flask. To this solution is added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.128 mmol) and Cu(OAc)$_2$ (catalytic). The mixture is stirred overnight. The reaction mixture is quenched with saturated aqueous NaHCO$_3$ and extracted 4× with CH$_2$Cl$_2$. The organic extracts are combined and dried over anhydrous Na$_2$SO$_4$. The mixture is filtered and concentrated in vacuo. The products are isolated by first by radial chromatography on silica gel affording 17-ethyl-1,14-dihydroxy-12-[2'-(3''-(3''',4'''-dimethylphenylo xy)-4'''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 12

A. 17-Ethyl-1,14-dihydroxy-12-[2'-(3''-(4'''-methoxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4''-(4'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(4-methoxyphenyl)bismuthine (136 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone). Each compound was repurified 2× by preparative TLC on silica gel (3:1 hexanes/acetone then 3.5% MeOH/CH$_2$Cl$_2$) affording 23.4 mg of 17-ethyl-1,14-dihydroxy-12-[2'-(4''-(4'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 28.4 mg of 17-ethyl-1,14-dihydroxy-12-[2'-(3''-(4'''-methoxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structures).

EXAMPLE 13

A. 17-Ethyl-1,14-dihydroxy-12-[2'-(3''-(3'''-methoxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(3-methoxyphenyl)bismuthine (136 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone). Each compound was repurified 2× by preparative TLC on silica gel (2:1 hexanes/acetone then 3.5% MeOH/CH$_2$Cl$_2$) affording 27 mg of 17-ethyl-1,14-dihydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 35 mg of 17-ethyl-1,14-dihydroxy-12-[2'-(3''-(3'''-methoxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structures).

EXAMPLE 14

A. 17-Ethyl-1,14-dihydroxy-12-[2'-(3''-(4'''-tert-butyldimethylsilyloxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4''-(4'''-tert-butyldimethylsilyloxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(4-tert-butyldimethylsilyloxyphenyl)bismuthine (213 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone) affording 41.9 mg. of 17-ethyl-1,14-dihydroxy-12-[2'-(4''-(4'''-tert-butyldimethylsilyloxy-phenyloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone and 42.5 mg. of 17-ethyl-1,14-dihydroxy-12-[2'-(3''-(4'''-tert-butyldimethylsilyloxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structures).

EXAMPLE 15

17-Ethyl-1,14-dihydroxy-12-[2'-(3''-(4'''-hydroxyphenyloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(3''-(4'''-tert-butyldimethylsilyloxyphenyloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (42.5 mg) in CH$_2$Cl$_2$ (1.5 mL.) at 0° C. was added a solution of p-toluenesulfonic acid in methanol (1.5 mL. of a 10% w/v solution). The mixture was stirred 3H at 0° C. and then 3H at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) affording 25.7 mg of 17-ethyl-1,14-dihydroxy-12-[2'-(3''-(4'''-hydroxyphenyloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 16

17-Ethyl-1,14-dihydroxy-12-[2'-(4''-(4'''-hydroxyphenyloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4''-(4'''-tert-butyldimethylsilyloxyphenyloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (41.9 mg) in CH$_2$Cl$_2$ (1.5 mL.) at 0° C. was added a solution of p-toluenesulfonic acid in methanol (1.5 mL. of a 10% w/v solution). The mixture was stirred 3H at 0° C. and then 3H at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) affording 23.9 mg of 17-ethyl-1,14-dihydroxy-12-[2'-(4''-(4'''-hydroxyphenyloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis are consistent with the desired structure).

EXAMPLE 17

A. 17-ethyl-1,14-dihydroxy-12-[2'-(3''-(6'''-tert-butyldimethylsilyloxynaphth-2-yloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 17-Ethyl-1,14-dihydroxy-12-[2'-(4''-(-4'''-tert-butyldimethylsilyloxy-naphth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(6-tert-butyldimethylsilyloxynaphth-2-yl)bismuthine (252 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone) affording 39.8 mg. of 17-ethyl-1,14-dihydroxy-12-[2'-(4''-(4'''-tert-butyldimethylsilyloxyphenyloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone and 41.6 mg. of 17-ethyl-1,14-dihydroxy-12-[2'-(3''-(4'''-tert-butyldimethylsilyloxyphenyloxy)-4''-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone. ($^1$H NMR and mass spectral analysis were consistent with the desired structures).

EXAMPLE 18

17-Ethyl-1,14-dihydroxy-12-[2'-(4''-(6'''-hydroxynaphth-2-yloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4''-(6'''-tert-butyldimethylsilyloxynaphth-2-yloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (39.8 mg) in CH$_2$Cl$_2$ (1.5 mL.) at 0° C. was added a solution of p-toluenesulfonic acid in methanol (1.5 mL. of a 10% w/v solution). The mixture was stirred 1.25 h at 0° C. and then 1.75 h at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted 2× with 2:1 hexanes/acetone) affording 17 mg of 17-ethyl-1,14-dihydroxy-12-[2'-(4''-(6'''-hydroxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 19

17-Ethyl-1,14-dihydroxy-12-[2'-(3''-(6'''-hydroxynaphth-2-yloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(3''-(6'''-tert-butyldimethylsilyloxynaphth-2-yloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (41.6 mg) in CH$_2$Cl$_2$ (1.5 mL.) at 0° C. was added a solution of p-toluenesulfonic acid in methanol (1.5 mL. of a 10% w/v solution). The mixture was stirred 1.25 h at 0° C. and then 1.75 h at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted 2× with 2:1 hexanes/acetone) affording 20.8 mg of 17-ethyl-1,14-dihydroxy-12-[2'-(3''-(6'''-hydroxynaphth-2-yloxy)-4''-hydroxycyclohexyl)-1'-methylvinyl]23,25-dimethoxy-13,19,21,27-tetramethyl-11,28-dioxa-4-azatricyclo [22.3.1.0$^{4,9}$]octacos-18-ene-2,3,10,16-tetraone. ($^1$H NMR and mass spectral analysis were consistent with the desired structure).

EXAMPLE 20

17-Ethyl-1,14-dihydroxy-1-2-[2'-(3'''-(1''',4'''-benzodioxane-6-yl)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(1,4-benzodioxan-6-yl)bismuthine (90 mg, 0.146 mmol) in CH$_2$Cl$_2$ (1 mL) is added peracetic acid (0.030 mL, 0.13 mmol, 32 wt % in dilute acetic acid). After 20 minutes the mixture is treated with 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) followed by Cu(OAc)$_2$ (15 mg, 0.08 mmol) and stirred for several days. The reaction mixture is quenched with saturated aqueous NaHCO$_3$ and extracted with CH$_2$Cl$_2$. The extracts are combined, dried with Na$_2$SO$_4$, filtered and concentrated in vacuo. The product is purified by preparative TLC on silica gel to give 17-ethyl-1,14-dihydroxy-12--[2'-(3''-(1''',4'''-benzodioxane-6-yl)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 21

A. 17-Ethyl-1-hydroxy-12-[2'-(4''-phenoxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,18,16-tetraone and B. 17-Ethyl-1-hydroxy-12-[2'-(4''-hydroxy-3''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Acetic acid (0.136 ml) was added to a solution of triphenylbismuth carbonate in dichloromethane (4.6 ml) at room temperature under a nitrogen atmosphere and the resulting solution stirred for 20 minutes. This was added to a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (296 mg) in dichloromethane (5.5 ml) containing cupric acetate (13 mg) and stirred at room temperature for 6 hours. The reaction mixture was washed with saturated sodium bicarbonate solution and the aqueous layer re-extracted with ether (2×25 ml). The combined organics were dried (MgSO$_4$) and concentrated to give the crude phenylated isomer mixture. These were separated by column chromatography on silica gel eluting with 70% hexane:30% ethyl acetate to give title compounds (4''-ether:93 mg, 28%) and (3''-ether:102 mg, 31%) each as white solids. ($^1$H NMR analysis were consistent with the desired structures).

EXAMPLE 22

17-Ethyl-1-hydroxy-12-[2'-(3''-azido-4''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-Ethyl-1-hydroxy-12-[2'-(4''-phenoxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (63 mg) was treated with diisopropylethylamine (0.079 ml) followed by 4-dimethylaminopyridine (37 mg) in dichloromethane solution at 0° C. Trifluoromethanesulphonic anhydride (0.051 ml) was then added slowly immediately forming a deep purple solution which was stirred at 0° C. for 45 minutes. The reaction mixture was then filtered through a pad of silica gel, rinsing with ethyl acetate, and concentrated. The residue was diluted with dry dimethylformamide (1.5 ml), treated with sodium azide (15 mg) and heated at 60° C. for 1 hour. The reaction mixture was diluted with dichloromethane, washed with brine, dried (MgSO$_4$) and concentrated. Purified by column chromatography on silica gel eluting with 60% hexane:40% ethyl acetate to give the title compound as a white solid (24 mg, 37%). ($^1$H NMR analysis was consistent with the desired structure).

EXAMPLE 23

17-Ethyl-1-hydroxy-12-[2'-(4''-azido-3''-phenoxycyclohexyl)-1'-methylvinyl]-23,25-dimethoxy-13,19,21,27-tetramethyl-11,28-dioxa-4-azatricyclo[23.3.1.0$^{4,9}$]octacos-18-ene-2,3,10,16-tetraone 17-Ethyl-1-hydroxy-12-[2'-(4''-hydroxy-3''-phenoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (84 mg) was treated with diisopropylethylamine (0.104 ml) followed by 4-dimethylaminopyridine (49 mg) in dichloromethane solution at 0° C. Trifluoromethanesulphonic anhydride (0.067 ml) was then added slowly immediately forming a deep purple solution which was stirred at 0° C. for 45 minutes. The reaction mixture was then filtered through a pad of silica gel, rinsing with ethyl acetate, and concentrated. The residue was diluted with dry dimethylformamide (2 ml), treated with sodium azide (20 mg) and heated at 60° C. for 1 hour. The reaction mixture was diluted with dichloromethane, washed with brine, dried (MgSO$_4$) and concentrated. Purified by column chromatography on silica gel eluting with 60% hexane:40% ethyl acetate to give the title compound as a white solid (43 mg, 50%). ($^1$H NMR analysis was consistent with the desired structure).

EXAMPLE 24

17-Ethyl-1-hydroxy-12-[2'-(3"-amino-4"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-Ethyl-1-hydroxy-12-[2'-(3"-azido-4"-phenoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (24 mg) in THF (1 ml) containing 1 drop of water was treated with triphenylphosphine (9 mg) and the mixture stirred at room temperature for 72 hours. The reaction mixture was purified directly by preparative thin layer chromatography eluting eith 90% dichloromethane:10% methanol to give the title compound (5 mg, 20%) as a white solid. ($^1$H NMR analysis was consistent with the desired structure).

EXAMPLE 25

17-Ethyl-1-hydroxy-12-[2'-(4'''-amino-3''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-Ethyl-1-hydroxy-12-[2'-(4'''-azido-3''-phenoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (64 mg) in THF (1.5 mml) containing 1 drop of water was treated with triphenylphosphine (24 mg) and the mixture stirred at room temperature for 72 hours. The reaction mixture was purified directly by preparative thin layer chromatography eluting with 90% dichloromethane:10% methanol to give the title compound (43 mg, 68%) as a white solid. ($^1$H NMR analysis was consistent with the desired structure).

EXAMPLE 26

17-Ethyl-1-hydroxy-12-[2'-(4"-acetylamino-3"-p-henoxycyclohexyl)-1'-methylvinyl]-23,25-dimethoxy-13,19,21,27-tetramethyl-11,28-dioxa-4-azatricyclo[22.31.0$^{4,9}$]octacos-18-ene-2,3,20,26-tetraone To a solution of 17-ethyl-1-hydroxy-12-[2'-(4"-amino-3"-phenoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (30 mg) in dry methylene chloride (0.2 ml) is added triethylamine (10 μl) followed by a solution of acetic anhydride in methylene chloride (10 mg in 1 ml) at r.t. Reaction is stirred for 30 minutes and the solvent removed under nitrogen flow. The crude product is purified by preparative tlc on silica gel to give of the title compound.

EXAMPLE 27

17-Ethyl-1-hydroxy-12-[2'-(4"-N-(2-propenyl)-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The compound 17-ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (31 mg) is placed in a dry flask equipped with stir bar and condenser. Dry toluene (1 ml) is added followed by diisopropylethylamine (13 mg) and freshly distilled allyl bromide (41 mg) at 0° C. with stirring. Reaction temperature is raised to 70° C. gradually and stirred for 2 hr. The reaction mixture is cooled, and the solvent is removed under nitrogen flow. The residue is purified by preparative tlc on silica gel to give the title compound.

EXAMPLE 28

17-Ethyl-1-hydroxy-12-[2'-[4"-(N'-t-butoxy-carbonyl-D-phenylalanine)amido-3"-phenoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-amino-3"-phenoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (46 mg) in dry methylene chloride (2 ml) is added 102 mg of freshly prepared BOC-D-phenylalanine anhydride (prepared as described in *Solid Peptide Sythesis*, p. 32, J. M. Steward and J. D. Young, Pierce Chemical Company) under nitrogen. Reaction is stirred at room temperature and the process is followed by tlc analysis. After 2.5 hr, the reaction mixture is subjected to work-up and preparative tlc on silica gel to give the title compound.

EXAMPLE 29

17-Ethyl-1-hydroxy-12-[2'-[4"-(N'-t-butoxy-carbonyl-L-phenylalanine)amido-3"-phenoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the method of Example 28 utilizing BOC-L-phenylalanine anhydride.

EXAMPLE 30

17-Ethyl-1-hydroxy-12-[2'-(4"-acetoxyacetylamino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (42 mg) in dry methylene chloride (0.4 ml) is cooled to 0° C. To this solution is added a solution of acetoxyacetyl chloride (9 mg) in methylene chloride (0.5 ml). The reaction mixture is stirred at 0° C. for 30 minutes, and quenched with a drop of methanol. Purification by preparative tlc on silica gel gives the title compound.

EXAMPLE 31

17-Ethyl-1-hydroxy-12-[2'-(4"-1""-adamantane-carboxamido-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (37 mg) in dry methylene chloride (0.4 ml) is cooled to 0° C. To this solution is added triethylamine (10 μl) followed by a solution of 1-adamantane carbonyl chloride (10 mg) in methylene chloride (0.1 ml). The reaction mixture is stirred at 0° C. for 20 minutes. The reaction is purified by preparative tlc on silica gel to give the title compound.

EXAMPLE 32

17-Ethyl-1-hydroxy-12-[2'-(4"-cyclopropanecarboxamido-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 34 mg of 17-ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in dry methylene chloride (0.4 ml) is cooled to 0° C. To this solution is added triethylamine (10 μl) followed by a solution of cyclopropane carbonyl chloride (5 mg) in methylene chloride (0.1 ml). The reaction mixture is stirred at 0° C. for 30 min. The reaction mixture is purified by preparative tlc on silica gel to give the title compound.

EXAMPLE 33

17-Ethyl-1-hydroxy-12-[2-(4"-formamido-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The compound 17-ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) is mixed with methyl formate (0.5 ml) and is stirred at 0° C. for 1 hr. The reaction mixture is allowed to warm to room temperature and then is stirred overnight. The excess methylformate is removed with nitrogen flow and the crude mixture is purified by preparative tlc on silica gel to give the title compound.

EXAMPLE 34

17-Ethyl-1-hydroxy-12-{2'-[4''',5''''-dicarboethoxy-1'-'',2''',3'''-triazole)-3"-phenoxycyclohexyl]-1'-methylvinyl}-23,23-dimethoxy-13,19,21,27-tetramethyl-11,28-dioxa-4-azatricyclo[22.3.1.0$^{4,9}$]octacos-18-ene-2,3,10,16-tetraone A mixture of 17-ethyl-1-hydroxy-12-[2'-(4"-azido-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg) in neat diethylacetylene dicarboxylate (0.1 ml) is stirred at room temperature overnight. The cycloaddition product is isolated by preparative tlc on silica gel to give the title compound.

EXAMPLE 35

17-Ethyl-1-hydroxy-12-[2'-(3"-phenoxy-4"'-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (−78° C.) of oxalyl chloride is added dimethyl sulfoxide dropwise, followed by a solution of 17-ethyl-1-hydroxy-12-[2'-(4"-hydroxy-3'-phenoxycyclohexyl)-1'-methylvinyl]-14-triisopropylsiloxy-23,25-dimethoxy-13,19,21,27-tetramethyl-11,28-dioxa-4-azatricyclo[22.3.1.0$^{4,9}$]octacos-18-ene-2,3,10,16-tetraone in dry methylene chloride. The reaction mixture is stirred for 30 min. at −78° C. and then triethylamine is added. The reaction temperature is raised to room temperature, reaction was poured into water, and extracted with ethyl acetate (three times). Combined organic layers are washed (water, sat'd NaHCO$_3$), dried (anhydrous Na$_2$SO$_4$), and filtered. Removal of solvent followed by purification (silica gel column chromatography) gives the title compound.

EXAMPLE 36

17-Ethyl-1,14-dihydroxy-12-[2'-(3"-phenoxy-4"-oxocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-(3"-phenoxy-4"-oxocyclohexyl)-1'-methylvinyl]14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone in acetonitrile was added hydrofluoric acid at room temperature. The reaction progress is monitored by tlc analysis and then the reaction mixture is quenched with sat'd aqueous sodium bicarbonate. The organic layer is separated and the aqueous layer is extracted with ethyl acetate three times. Combined organic layers are washed (sat'd NaHCO$_3$, sat'd NaCl), dried (anhydrous Na$_2$SO$_4$), and filtered. Removal of solvent followed by purification (silica gel column chromatography, 50% ethyl acetate/hexane) gives the title compound.

EXAMPLE 37

17-Ethyl-1,14-dihydroxy-12-[2'-(4"-benzylamino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3"-phenoxy-4"-oxocyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in dry isopropyl alcohol (3 ml) is added benzyl amine (87 mg). The mixture is stirred at r.t. for 30 minutes, and cooled to −78° C. To this solution is added a solution of sodium cyanoborohydride (6.7 mg) in isopropyl alcohol (0.5 ml). The reaction is stirred at −78° C. and poured into ice water. Extraction with ethyl acetate, followed by purification gives the title compound as a mixture of epimers at C-4".

EXAMPLE 38

17-Ethyl-1-hydroxy-12-[2'-(4"-trimethylamino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Iodide 17-Ethyl-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is dissolved in absolute ethanol in a heavy walled glass tube. Methyl iodide (large excess) and NaHCO$_3$ are added, the tube is sealed, and then the tube is heated. Progress of the reaction is followed by watching disappearance of the starting amine on thin layer chromatography and the appearance of a more polar new spot. Upon completion of reaction, the quarternary iodide is obtained by evaporation of excess methyl iodide and solvent.

EXAMPLE 39

17-Ethyl-1,2-dihydroxy-12-[2'-(4''-acetylamino-3''-p-henoxycyclohexyl)-1'-methylvinyl]-23,25-dimethoxy-13,19,27-tetramethyl-11,28-dioxa-4-azatricyclo[22.3.1.0^4,9]octacos-18-ene-3,10,16-trione To a suspension of samarium iodide (63 mg) in dry THF (1 ml) is added a solution of diiodoethane (56 mg in 1 ml THF) at r.t., and stirred for 1 hr. The dark blue solution is cooled to −78° C., and to this mixture is added a solution of 17-ethyl-1-hydroxy-12-[2'-(4''-acetylamino-3''-phenoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (170 mg) in 50% THF/MeOH (3 ml). The reaction is stirred for −78° C. for 10 minutes., allowed to warm to room temperature over a period of 10 min., and then quenched with saturated potassium carbonate solution. The organic layer is extracted with ether/ethyl acetate, washed (sat'd NaCl), and dried (anhydrous Na$_2$SO$_4$). Removal of solvent followed by chromatography on silica gel gives the title compound.

EXAMPLE 40

17-Ethyl-1-hydroxy-12-{2'-[4''-(N'-phenylaminocarbonyl)amino-3''-phenoxycyclohexy]-1'-methylvinyl}-23,25-dimethoxy-13,19,21,27-tetramethyl-11,28-dioxa-4-azatricyclo[22.3.1.0^4,9]octacos-18-ene-2,3,10,16-tetraone To a solution of 17-ethyl-1-hydroxy-12-[2'-(4''-amino-3''-phenoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (40 mg) in methylene chloride (2 ml) is added phenyl isocyanate (12 mg) at 0° C. with stirring. The reaction mixture is warmed to room temperature and the reaction progress is followed by tlc analysis. The reaction mixture is concentrated under a stream of nitrogen and purified by preparative tlc on silica to give the title compound.

EXAMPLE 41

17-Ethyl-1-hydroxy-12-{2'-[4''-(ethoxycarbonyl)amino-3''-phenoxycyclohexyl]-1'-methylvinyl}-23,25-dimethoxy-13,19,21,27-tetramethyl-11,28-dioxa-4-azatri-cyclo[22.3.1.0^4,9]otacos-18-ene-2,3,10,16-tetraone To a solution of 17-ethyl-1-hydroxy-12-[2'-(4''-amino-3''-phenoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (40 mg) in methylene chloride (2 ml) is added triethylamine (10 µl), followed by ethyl chloroformate (15 µl) at 0° C. with stirring. The reaction mixture is warmed to room temperature and the reaction progress is followed by tlc analysis. the solution is quenched with a drop of methanol and purified by preparative tlc on silica to give the title compound.

EXAMPLE 42

17-Ethyl-1-hydroxy-12-[2'-(4''-(2'''R-hydroxypropyl)amino-3''-phenyloxycyclohexyl)-1'-methylvinyl]-23,25-dimethoxy-13,19,21,27-tetramethyl-11,28-dioxa-4-azatricyclo[22.3.1.0^4,9]-octacos-18-ene-2,3,10,16-tetraone To a solution of 17-Ethyl-1-hydroxy-12-[2'-(4''-amino-3''-phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone (19 mg) in methanol (1 ml) at ambient temperature was added R-(+)-propylene oxide (85 ml) and the mixture stirred for 46 hrs. The reaction was quenched by the addition of saturated sodium bicarbonate solution and extracted into ether. The crude mixture was purified by column chromatography on silica gel eluting with 97% methylene chloride: 3% methanol to give the title compound (11 mg) as a white solid.

MS(FAB) 895(M+) partial $^1$H NMR d: 7.25 (m, 2H); 6.90 (m, 2H); 4.52 (d, J=6 Hz, 1H); 3.85 (d, J=9, 2 Hz, 1H).

EXAMPLE 43

17-Ethyl-1-hydroxy-12-[2'-(4''-(2'''S-hydroxypropyl)amino-3''-phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above example using S-(−)-propylene oxide as the amine alkylating agent.

MS(FAB) 895(M+) partial $^1$H NMR d: 7.25 (m, 2H); 6.90 (m, 2H); 4.52 (d, J=6 Hz, 1H); 3.85(d, 9 Hz).

EXAMPLE 44

17-Ethyl-1-hydroxy-12-[2'-(4''-(2''-''R-hydroxypropyl)amino-3''-(4'''-methyl)phenyloxycyclohexyl)-1'-methylvinyl]-23,25-dimethoxy-13,19,21,27-tetra-methyl-11,28-dioxa-4-azatricyclo[22.3.1.04,9]-octacos-18-ene-2,3,10,16-tetraone Prepared essentially as described in the above example using R-(−)-propylene oxide as the amine alkylating agent.

MS(FAB) 910(M++1) partial $^1$H NMR d: 7.15 (d, J=9 Hz, 2H); 6.78 (d, J=9 Hz, 2H); 4.52 (d, J=6 Hz, 1H); 2.24 (s, 3H).

EXAMPLE 45

17-Ethyl-1-hydroxy-12-[2'-(4''-(2''-''S-hydroxypropyl)amino-3''-(4'''-methyl)phenyloxycyclohexyl)-1'-methylvinyl]-23,25-dimethoxy-13,19,21,27-tetra-methyl-11,28-dioxa-4-azatricyclo[22.3.1.04,9]-octacos-18-ene-2,3,10,16-tetraone Prepared essentially as described in the above example using S-(−)-propylene oxide as the amine alkylating agent.

MS(FAB) 910(M++1) partial $^1$H NMR d: 7.05 (d, J=9 Hz, 2H); 6.79 (d, J=9 Hz, 2H); 4.52 (d, J=6 Hz, 1H); 2.24 (s, 3H).

EXAMPLE 46

17-Ethyl-1-hydroxy-12-[2'-(4"-(2"'- 'R-hydroxypropyl)amino-3"-(4"'-methoxy)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone Prepared essentially as described in the above example using R-(−)-propylene oxide as the amine alkylating agent.

MS(FAB) 925(M+) partial ¹H NMR d: 6.80 (m, 4H); 3.96 (d, J=6 Hz, 1H); 3.72 (s, 3H).

EXAMPLE 47

17-Ethyl-1-hydroxy-12-[2'-(4"-(2"'- 'S-hydroxypropyl)amino-3"-(4"'-methoxy)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone Prepared essentially as described in the above example using S-(−)-propylene oxide as the amine alkylating agent.

MS(FAB) 925(M+) partial ¹H NMR d: 6.82 (m, 4H); 3.83 (d, J=7 Hz, 1H); 3.72 (s, 3H).

EXAMPLE 48

17-Ethyl-1-hydroxy-12-[2'-(4"-(2"'R-hydroxypropyl)amino-3"-allyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone Prepared essentially as described in the above example using R-(−)-propylene oxide as the amine alkylating agent.

MS(FAB) 860(M++1) partial ¹H NMR d: 5.85 (m, 1H); 4.52 (d, J=6 Hz, 1H); 3.97 (d, J=6 Hz, 1H).

EXAMPLE 49

17-Ethyl-1-hydroxy-12-[2'-(4"-(2"'S-hydroxypropyl)amino-3"-allyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone Prepared essentially as described in the above example using S-(−)-propylene oxide as the amine alkylating agent.

MS(FAB) 860(M++1) partial ¹H NMR d: 5.89 (ddd, J=22,10,6 Hz, 1H); 4.53 (d, J=6 Hz, 1H); 3.99 (d, J=6 Hz, 1H).

EXAMPLE 50

17-Ethyl-1-hydroxy-12-[2'-(4"-dimethylamino-3"-(3"'-methoxy)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone To a solution of 17-Ethyl-1-hydroxy-12-[2'-(4"-amino-3"-(3"'-methoxy)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone (25 mg) in tetrahydrofuran was added aqueous formaldehyde solution (36%) (66 ml) and the reaction stirred until t.l.c. indicated disappearance of starting material. At this point 2 drops of acetic acid were added followed by 66 ml of sodium cyanoborohydride solution in methanol (7 mg/ml). When complete the reaction was quenched by the addition of saturated sodium bicarbonate solution and extracted into ethyl acetate and dichloromethane. The organic extracts were dried, concentrated and purified by preparative chromatography eluting with 95% dichloromethane: 5% methanol+1% ammonium hydroxide to give the product (5 mg) as a white solid.

MS(FAB) 895(M++1) partial ¹H NMR d: 7.11 (m, 2H); 6.42 (m, 2H); 3.73 (s, 6H).

EXAMPLE 51

17-Ethyl-1-hydroxy-12-[2'-(4"-(4"'-dimethylamino)phenyloxy-3"-hydroxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone (A) and 17-Ethyl-1-hydroxy-12-[2'-(4"-hydroxy-3"-(4"'-dimethylamino)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone (B)

Peracetic acid (850 ml) was added to a solution of tri(4-dimethylaminophenyl)bismuthine (1.27 g) in 30 ml tetrahydrofuran. After 10 minutes 17-ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone (100 mg) was added followed by copper acetate (280 mg) and the mixture heated to 60° C. for 48 hours. The mixture was then cooled and quenched by pouring into saturated sodium bicarbonate, extracting with ether (3×25 ml). The combined organic washes were dried with magnesium sulphate and concentrated. The crude residue was purified by column chromatography on silica gel eluting with 70% hexane: 30% ethyl acetate to give the title compounds A (93 mg) and B (102 mg) each as white solids.

EXAMPLE 52

17-Ethyl-1-hydroxy-12-[2'-(4"'-azido-3"-(4"'-dimethylamino)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone 17-Ethyl-1-hydroxy-12-[2'-(4"-hydroxy-3"-(4"'-dimethylamino)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone (84 mg) was treated with diisopropylethylamine (0.104 ml) followed by 4-dimethylaminopyridine (49 mg) in dichloromethane solution at 0° C. Trifluoromethanesulphonic anhydride (0.067 ml) was then added slowly immediately forming a deep purple solution which was stirred at 0° C. for 45 minutes. The reaction mixture was then filtered through a pad of silica gel, rinsing with ethyl acetate, and concentrated. The residue was diluted with dry dimethylformamide (2 ml), treated with sodium azide (20 mg) and heated at 60° C. for 1 hour. The reaction mixture was diluted with dichloromethane, washed with brine, dried (MgSO4) and concentrated. Purified by column chromatagraphy on silica gel eluting with 60% hexane: 40% ethyl acetate to give the title compound as a white solid (43 mg).

EXAMPLE 53

17-Ethyl-1-hydroxy-12-[2'-(4"-amino-3"-(4'"-dimethylamino)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone 17-Ethyl-1-hydroxy-12-[2'-(4"-azido-3"-(4'"-dimethylamino)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone (64 mg) in benzene (4 ml) containing 500 ml of water was treated with triphenylphosphine (125 mg) and the mixture heated to 60° C. for 17 hours. The mixture was cooled, concentrated and purified by column chromatography on silica gel eluting with 98% dichloromethane: 2% methanol to give the title compound (43 mg) as a white solid.

MS(FAB) 880(M+) partial 1H NMR d: 7.82 (d, J=8 Hz, 2H); 7.66 (d, J=8 Hz, 2H); 5.17 (m, 1H), 2.82 (s, 3H), 2.81 (s, 3H).

EXAMPLE 54

17-Ethyl-1-hydroxy-12-[2'-(4"-amino-3"-(4'"-methyl)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above examples using tri(4-methylphenyl)bismuthine as the arylating agent.

MS(FAB) 851(M+) partial 1H NMR d: 7.04 (d, J=7 Hz, 2H); 6.77 (d, J=7 Hz); 5.16 (m, 1H); 2.23 (s, 3H).

EXAMPLE 55

17-Ethyl-1-hydroxy-12-[2'-(4"-amino-3"-(4'"-hydroxymethyl)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above examples using tri(4-hydroxymethylphenyl)bismuthine as the arylating agent.

MS(FAB) 867(M++1) partial 1H NMR d: 7.25 (m, 2H); 6.88 (m, 2H); 5.21d(minor) and 5.17d(major) (J=6.5 Hz, 1H); 4.59 (d, J=2 Hz, 2H).

EXAMPLE 56

17-Ethyl-1-hydroxy-12-[2'-(4"-amino-3"-(4'"-methoxy)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above examples using tri(4-methoxyphenyl)bismuthine as the arylating agent.

MS(FAB) 867(M+) partial 1H NMR d: 6.81 (m, 4H); 5.20 (m,major and minor, 1H); 3.72 (s,major) and 3.71 (s, minor)(3H).

EXAMPLE 57

17-Ethyl-1-hydroxy-12-[2'-(4"-amino-3"-(3'"-methoxy)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above examples using tri(3-methoxyphenyl)bismuthine as the arylating agent.

MS(FAB) 868(M++1) partial 1H NMR d: 7.15 (m, 2H); 6.50 (m, 3H); 3.74 (s, 3H).

EXAMPLE 58

17-Ethyl-1-hydroxy-12-[2'-(4"-amino-3"-(4'"-hydroxy)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above examples using tri(4-hydroxyphenyl)bismuthine as the arylating agent.

MS(FAB) 853(M+) partial 1H NMR d: 6.72 (m, 4H); 5.27d(minor) and 5.18d(major) (9 Hz, 1H); 4.85 (m, 1H).

EXAMPLE 59

17-Ethyl-1-hydroxy-12-[2'-(4"-amino-3"-(4'"-formyl)phenyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone Prepared essentially as described in the above examples using tri(4-formylphenyl)bismuthine as the arylating agent.

partial 1H NMR d: 9.86 (s, 1H); 7.80 (d, J=9 Hz, 2H); 6.98 (d, J=9 Hz, 2H).

EXAMPLES 60-85

Utilizing the general procedures described in Examples 1 to 59, the following compounds of Formula I (wherein $R^4$ is hydrogen, and n is 2) are prepared from the appropriately substituted starting materials and reagents.

| EXAMPLE NO. | $R^2$ | $R^1$ | $R^3$ | $R^5$ |
| --- | --- | --- | --- | --- |
| 60 | HO-C6H4- | NH$_2$ | H | CH$_3$CH$_2$ |
| 61 | HO-C6H4- | NH$_2$ | OH | CH$_3$CH$_2$ |

-continued

| EXAMPLE NO. | R² | R¹ | R³ | R⁵ |
|---|---|---|---|---|
| 62 | 4-HO-C₆H₄- | NH₂ | H | CH₂=CHCH₂- |
| 63 | 3,4-(CH₃O)₂-C₆H₃- | NH₂ | OH | CH₃CH₂CH₂ |
| 64 | 4-HOCH₂-C₆H₄- | NH₂ | OH | CH₃CH₂ |
| 65 | 4-HO₂C-C₆H₄- | NH₂ | H | CH₃CH₂ |
| 66 | 4-CF₃-C₆H₄- | NH₂ | OH | CH₃CH₂CH₂ |
| 67 | 3-CH₃O-4-HO-C₆H₃- | NH₂ | H | CH₂=CHCH₂- |
| 68 | 3-CH₃O-4-HO-C₆H₃- | (CH₃)₂N | OH | CH₃CH₂ |
| 69 | 4-CH₃C(O)O-C₆H₄- | NH₂ | H | CH₂CH₃ |
| 70 | 4-CH₃SO-C₆H₄- | NH₂ | OH | CH₃CH₂ |
| 71 | 4-CH₃SO₂-C₆H₄- | (CH₃)₂N | OH | CH₂CH₃ |
| 72 | 4-CH₃O-C₆H₄- | NH₂ | OH | CH₂CH₃ |
| 73 | 4-CH₃O-C₆H₄- | NH₂ | H | CH₃CH₂ |

-continued
| EXAMPLE NO. | R² | R¹ | R³ | R⁵ |
|---|---|---|---|---|
| 74 | NH₂ | 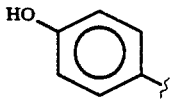 4-HO-C₆H₄- | H | CH₃CH₂ |
| 75 | NH₂ | 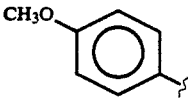 4-CH₃O-C₆H₄- | H | CH₃CH₂ |
| 76 | 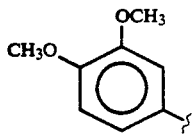 3,4-(CH₃O)₂-C₆H₃- | NH₂ | OH | CH₃CH₂ |
| 77 | NH₂ | 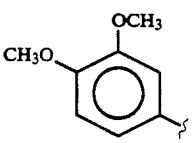 3,4-(CH₃O)₂-C₆H₃- | OH | CH₃CH₂ |
| 78 | 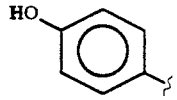 4-HO-C₆H₄- | (CH₃)₂N | OH | CH₃CH₂ |
| 79 | 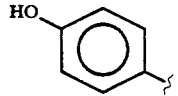 4-HO-C₆H₄- | (CH₃)₃N⁺ | OH | CH₃CH₂ |
| 80 | 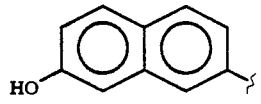 6-HO-naphth-2-yl | NH₂ | OH | CH₃CH₂CH₂ |
| 81 | 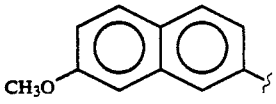 6-CH₃O-naphth-2-yl | NH₂ | H | CH₃CH₂ |
| 82 | 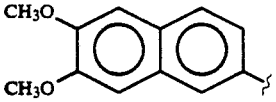 6,7-(CH₃O)₂-naphth-2-yl | NH₂ | H | CH₂=CHCH₂— |
| 83 | 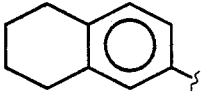 5,6,7,8-tetrahydronaphth-2-yl | NH₂ | OH | CH₃CH₂ |
| 84 | NH₂ | 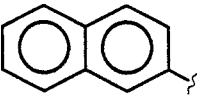 naphth-2-yl | H | CH₃CH₂ |
| 85 | NH₂ | 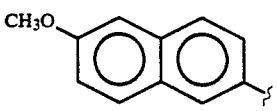 6-CH₃O-naphth-2-yl | H | CH₃CH₂ |

-continued

| EXAMPLE NO. | R² | R¹ | R³ | R⁵ |
|---|---|---|---|---|
| 86 | NH₂ | 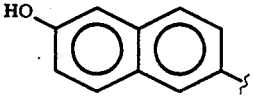 | H | CH₃CH₂ |

EXAMPLE 87

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone was used as a standard. The culture plates were then incubated at 37° C. in a humidified atmosphere of 5% CO₂-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:

24, 25, 42, 43, 44, 45, 46, 47, 48, 49, 50, 51, 52, 53, 54, 55, 56, 57, 58 and 59.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

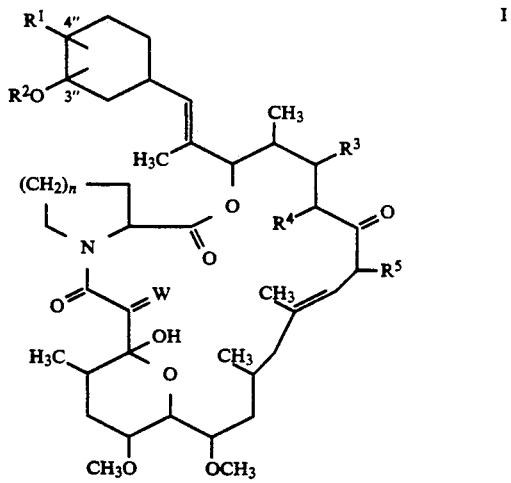

or a pharmaceutically acceptable salt thereof, wherein:
$R^1$ is selected from:
1) —N₃;
2) —NHCN;
3) —NR⁶R⁷, wherein R⁶ and R⁷ independently, are,
   a) hydrogen,
   b) C₁-C₁₂ alkyl, unsubstituted or substituted with R⁸ and R⁹, wherein R⁸ and R⁹ are independently selected from the group consisting of:
      i) hydrogen,
      ii) —OH,
      iii) C₁-C₆alkoxy,
      iv) —O—CO—C₁-C₆alkyl,
      v) —NR¹⁰R¹¹, wherein R¹⁰ and R¹¹ are independently, hydrogen, or C₁-C₆alkyl, unsubstituted or substituted with phenyl vi) —CONR$^{10}$R$^{11}$,
vii) —CO$_2$H,
viii) —CO—O—C$_1$-C$_6$alkyl,
ix) —S—C$_1$-C$_6$alkyl,
x) —SO—C$_1$-C$_6$alkyl,
xi) —SO$_2$—C$_1$-C$_6$alkyl,
xii) halo,
xiii) —C$_3$-C$_7$-cycloalkyl,
xiv) phenyl, unsubstituted or substituted with X, Y and Z,
xv) naphthyl, unsubstituted or substituted with X, Y and Z,
xvi) —CF$_3$,
c) C$_3$-C$_{12}$ alkenyl, unsubstituted or substituted with R$^8$ and R$^9$, wherein R$^8$ and R$^9$ are as defined above,
d) C$_3$-C$_7$ cycloalkyl, unsubstituted or substituted with R$^8$ and R$^9$, wherein R$^8$ and R$^9$ are as defined above,
e) phenyl, unsubstituted or substituted with X, Y and Z,
f) naphthyl, unsubstituted or substituted with X, Y and Z,
f) —SO$_2$-phenyl, wherein phenyl is unsubstituted or substituted with X, Y and Z,
h) —SO$_2$—C$_1$-C$_6$alkyl,
i) or where R$^6$ and R$^7$ and the N to which they are attached may form a heterocyclic ring, selected from the group consisting of: morpholine, thiomorpholine, piperidine, and piperazine, and where the substituent(s), attached to the carbon atom(s) in the heterocyclic ring is/are independently selected from the group consisting of:
i) hydrogen,
ii) —OH,
iii) C$_1$-C$_6$ alkoxy,
iv) —O—CO—C$_1$-C$_6$ alkyl,
v) —NR$^{10}$R$^{11}$, wherein R$^{10}$ and R$^{11}$ are independently, hydrogen, or C$_1$-C$_6$alkyl, unsubstituted or substituted with phenyl,
vi) —CONR$^{10}$R$^{11}$,
vii) —CO$_2$H,
viii) —CO—O—C$_1$-C$_6$ alkyl,
ix) —SH,
x) halo,
xi) phenyl, unsubstituted or substituted with X, Y and Z,
xii) naphthyl, unsubstituted or substituted with X, Y and Z,
xiii) —CF$_3$;
4) —N(R$^6$)CO—O—R$^{12}$, wherein R$^6$ is as defined above and R$^{12}$ is C$_1$-C$_{12}$ alkyl, unsubstituted or substituted with R$^8$ and R$^9$, wherein R$^8$ and R$^9$ are as defined above;
5) —N(R$^6$)CO—R$^{13}$, wherein R$^6$ is as defined above and R$^{13}$ is
a) hydrogen,
b) C$_1$-C$_{12}$ alkyl, unsubstituted or substituted with R$^8$ and R$^9$, wherein R$^8$ and R$^9$ are as defined above,
c) C$_3$-C$_{12}$ cycloalkyl, unsubstituted or substituted with R$^8$ and R$^9$, wherein R$^8$ and R$^9$ are as defined above,
d) phenyl, unsubstituted or substituted with X, Y and Z,
e) naphthyl, unsubstituted or substituted with X, Y and Z, or
f) where R$^6$ and R$^{13}$ and the —NCO— to which they are attached may form a heterocyclic ring selected from the group consisting of: pyrrolidone, and piperidinone;
6) —N(R$^{14}$)COCH(R$^{22}$)NR$^6$R$^7$ wherein R$^6$ and R$^7$ are as defined above, R$^{14}$ is selected from the definitions of R$^6$, and R$^{22}$ is
a) hydrogen,
b) C$_1$-C$_4$alkyl, unsubstituted or substituted with R$^{23}$ wherein R$^{23}$ is selected from the group consisting of:
i) —OH,
ii) C$_1$-C$_6$alkoxy,
iii) —O—CO—C$_1$-C$_6$alkyl,
iv) —SH,
v) —S—C$_1$-C$_6$alkyl,
vi) —NR$^{10}$R$^{11}$, wherein R$^{10}$ and R$^{11}$ are as defined above,
vii) —CO$_2$H,
viii) —CONH$_2$,
ix) imidazolyl,
x) indolyl,
xi) phenyl, and
xii) p-hydroxyphenyl, or,
c) phenyl;
7) —N(R$^{14}$)CO(CH$_2$)$_m$NR$^6$R$^7$, wherein m is 0 or 2-6, R$^6$ and R$^7$ are as defined above, and R$^{14}$ is selected from the definitions of R$^6$, or where R$^{14}$ and R$^6$ and the —NCO(CH$_2$)$_m$N— to which they are attached may form a heterocyclic ring, which is 2-imidazolidone;
8) —N=C(R$^{14}$)—NR$^6$R$^7$, wherein R$^6$ and R$^7$ are as defined above, and R$^{14}$ is selected from the definitions of R$^6$, and wherein if either R$^6$ or R$^7$ are hydrogen, the tautomeric structure —NHC(R$^{14}$)=NR$^{6 or 7}$ is also possible;
9) —N(R$^{15}$)$_3$+A$^-$, wherein R$^{15}$ is C$_1$-C$_6$ alkyl, unsubstituted or substituted with phenyl or naphthyl, and wherein A$^-$ is a counterion selected from the group consisting of: acetate, adipate, benzoate, benzenesulfonate, bisulfate, butyrate, citrate, camphorate, camphorsulfonate, ethanesulfonate, fumarate, hemisulfate, hemitartrate, heptanoate, hexanoate, hydrochloride, hydrobromide, hydroiodide, methanesulfonate, lactate, maleate, methanesulfonate, 2-naphthalenesulfonate, nitrate oxalate, pamoate, perchlorate, persulfate, picrate, pivalate, propionate, succinate, tartrate, tosylate, and undecanoate;
10)

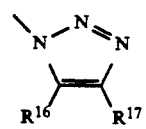

wherein R$^{16}$ and R$^{17}$ are independently,
a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_1$-C$_6$alkyl, or
g) —CO—O—C$_1$-C$_6$alkyl;

$R^2$ is selected from:
1) phenyl;
2) substituted phenyl in which the substituents are X, Y and Z;
3) 1- or 2- naphthyl;
4) substituted 1- or 2-naphthyl in which the substituents are X, Y and Z;
5) biphenyl;
6) substituted biphenyl in which the substituents are X, Y and Z;

$R^3$ is hydrogen, hydroxy, or $C_1$-$C_6$ alkoxy;

$R^4$ is hydrogen, or $R^3$ and $R^4$ taken together form a double bond;

$R^5$ is methyl, ethyl, propyl or allyl;

W is O or (H, OH);

X, Y and Z independently are selected from:
a) hydrogen,
b) $C_{1-7}$ alkyl,
c) $C_{2-6}$ alkenyl,
d) halo,
e) —$(CH_2)_p$—$NR^{10}R^{11}$, wherein $R^{10}$ and $R^{11}$ are, independently, hydrogen or $C_{1-6}$ alkyl, unsubstituted or substituted with phenyl and p is 0 to 2,
f) —CN,
g) —CHO,
h) —$CF_3$,
i) —$SR^{18}$, wherein $R^{18}$ is hydrogen, $C_{1-6}$alkyl, or phenyl,
j) —$SOR^{18}$, wherein $R^{18}$ is as defined above,
k) —$SO_2R^{18}$, wherein $R^{18}$ is as defined above,
l) —$CONR^{10}R^{11}$, wherein $R^{10}$ and $R^{11}$ are as defined above,
m) $R^{19}O(CH_2)_p$— wherein $R^{19}$ is hydrogen, $C_{1-3}$ alkyl, hydroxy-$C_{2-3}$alkyl, phenyl or naphthyl and p is as defined above;
n) —$CH(OR^{20})(OR^{21})$, wherein $R^{20}$ and $R^{21}$ are $C_{1-3}$alkyl or taken together form an ethyl or propyl bridge,
o)

wherein $R^{19}$ and p are as defined above, and
p)

wherein $R^{19}$ and p are as defined above; or any two of X, Y and Z may be joined to form a saturated ring selected from the group consisting of: dihydropyranyl, dihydrofuranyl, dioxolanyl and dioxanyl; and
n is 1 or 2.

2. The compound according to claim 1 wherein the steric configuration of formula I is as defined in formula III:

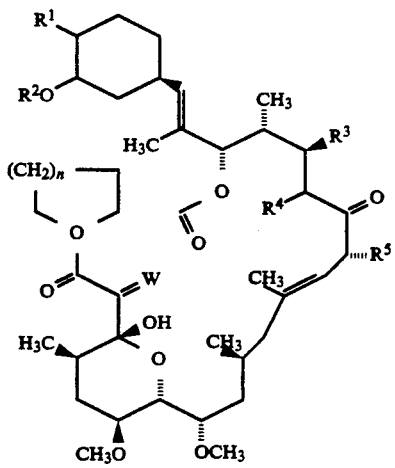

3. The compound according to claim 1 wherein:
$R^1$ is selected from:
1) —$N_3$;
3) —$NR^6R^7$, wherein $R^6$ and $R^7$ independently, are,
  a) hydrogen,
  b) $C_1$-$C_{12}$ alkyl, unsubstituted or substituted with $R^8$ and $R^9$, wherein $R^8$ and $R^9$ are independently selected from the group consisting of:
   i) hydrogen,
   ii) —OH,
   iii) —O—CO—$C_1$-$C_6$alkyl,
   iv) —$NR^{10}R^{11}$, wherein $R^{10}$ and $R^{11}$ are independently, hydrogen, or $C_1$-$C_6$alkyl, unsubstituted or substituted with phenyl
   v) —$CONR^{10}R^{11}$,
   vi) —$CO_2H$,
   vii) —CO—O—$C_1$-$C_6$alkyl,
   viii) phenyl, unsubstituted or substituted with X, Y and Z,
  c) $C_3$-$C_{12}$ alkenyl, unsubstituted or substituted with $R^8$ and $R^9$, wherein $R^8$ and $R^9$ are as defined above;
3) —$N(R^6)CO$—O—$R^{12}$, wherein $R^6$ is as defined above and $R^{12}$ is $C_1$-$C_{12}$ alkyl, unsubstituted or substituted with $R^8$ and $R^9$, wherein $R^8$ and $R^9$, wherein $R^8$ and $R^9$ are as defined above;
4) —$N(R^6)CO$—$R^{13}$, wherein $R^6$ is as defined above and $R^{13}$ is
  a) hydrogen,
  b) $C_1$-$C_{12}$alkyl, unsubstituted or substituted with $R^8$ and $R^9$, wherein $R^8$ and $R^9$ are as defined above,
  c) $C_3$-$C_{12}$ cycloalkyl, unsubstituted or substituted with $R^8$ and $R^9$, wherein $R^8$ and $R^9$ are as defined above,
  d) phenyl, unsubstituted or substituted with X, Y and Z,
5) —$N(R^{14})COCH(R^{22})NR^6R^7$ wherein $R^6$ and $R^7$ are as defined above, $R^{14}$ is selected from the definitions of $R^6$, and $R^{22}$ is
  a) hydrogen,
  b) $C_1$-$C_4$alkyl, unsubstituted or substituted with $R^{23}$ wherein $R^{23}$ is selected from the group consisting of:
   i) —OH,
   ii) $C_1$-$C_6$alkoxy, iii) —O—CO—C$_1$-C$_6$alkyl,
iv) —SH
v) —S—C$_1$-C$_6$alkyl,
vi) —NR$^{10}$R$^{11}$, wherein R$^{10}$ and R$^{11}$ are as defined above,
vii) —CO$_2$H,
viii) —CONH$_2$,
ix) imidazolyl,
x) indolyl,
xi) phenyl, and
xii) p-hydroxyphenyl, or
c) phenyl, 6) —N(R$^{14}$)CO(CH$_2$)$_m$NR$^6$R$^7$, wherein m is 0 or 2-6, R$^6$ and R$^7$ are as defined above, and R$^{14}$ is selected from the definitions of R$^6$, or where R$^{14}$ and R$^6$ and the —NCO(CH$_2$)$_m$N— to which they are attached may form a heterocyclic ring, which is 2-imidazolidone;

7) —N=C(R$^{14}$)—NR$^6$R$^7$, wherein R$^6$ and R$^7$ are as defined above, and R$^{14}$ is selected from the definitions of R$^6$, and wherein if either R$^6$ and R$^7$ are hydrogen, the tautomeric structure —NHC(R$^{14}$)=NR$^{6 or 7}$ is also possible;

8) —N(R$^{15}$)$_3^+$A$^-$, wherein R$^{15}$ is C$_1$-C$_6$ alkyl, unsubstituted or substituted with phenyl or naphthyl, and wherein A$^-$ is a counterion selected from the group consisting of: acetate, adipate, benzoate, benzenesulfonate, bisulfate, butyrate, citrate, camphorate, camphorsulfonate, ethanesulfonate, fumarate, hemisulfate, hemitartrate, heptanoate, hexanoate, hydrochloride, hydrobromide, hydroiodide, methanesulfonate, lactate, maleate, methanesulfonate, 2-naphthalenesulfonate, nitrate oxalate, pamoate, perchlorate, persulfate, picrate, pivalate, propionate, succinate, tartrate, tosylate, and undecanoate;

9)

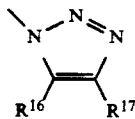

wherein R$^{16}$ and R$^{17}$ are independently,
a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_1$-C$_6$alkyl, or
g) —CO—O—C$_1$-C$_6$alkyl;

R$^2$ is selected from:
1) phenyl;
2) substituted phenyl in which the substituents are X, Y and Z;
3) 1- or 2-naphthyl;
4) substituted 1- or 2-naphthyl in which the substituents are X, Y and Z;

R$^3$ is hydrogen or hydroxy;
R$^4$ is hydrogen;
R$^5$ is ethyl, propyl or allyl;
W is O or (H, OH);
X, Y and Z independently are selected from:
a) hydrogen,
b) C$_{1-7}$ alkyl,
c) halo,
d) —CN,
e) —CHO,
f) —CF$_3$,
g) —CONR$^{10}$R$^{11}$, wherein R$^{10}$ and R$^{11}$ are as defined above,
h) R$^{19}$O(CH$_2$)$_p$-wherein R$^{19}$ is hydrogen, C$_{1-3}$ alkyl, hydroxy-C$_{2-3}$alkyl, phenyl or naphthyl and p is 0 to 2;
i) —CH(OR$^{20}$)(OR$^{21}$), wherein R$^{20}$ and R$^{21}$ are C$_{1-3}$alkyl or taken together form an ethyl or propyl bridge,
j)

wherein R$^{19}$ and p are as defined above;
k)

wherein R$^{19}$ and p are as defined above; or any two of X, Y and Z may be joined to form a saturated ring, selected from the group consisting of: dihydropyranyl, dihydrofuranyl, dioxolanyl and dioxanyl; and n is 1 or 2;
or a pharmaceutically acceptable salt thereof.

4. A compound which is selected from:
17-allyl-1,14-dihydroxy-12-[2'-(4''-amino-3''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1-hydroxy-12-[2'-(4''-amino-3''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-amino-3''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-amino-3''-phenoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-phenoxy-3''-aminocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4''-dimethylamino-3''-phenoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1-hydroxy-12-[2'-(4''-amino-3''-(4'''-methoxyphenoxy)cyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1-hydroxy-12-[2'-(4''-amino-3''-(4'''-hydroxyphenoxy)cyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1-hydroxy-12-[2'-(4'''-acetylamino-3''-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(4'''-fluorophenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-amino-3''-(4'''-carboxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(4'''-trifluoromethylphenoxy)cyclohexyl)-1'-methylvinyl]23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(3''',4'''-dimethoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-1,14-dihydroxy-12-[2'-(4''-amino-3''-(4'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(4'''-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-amino-3''-(4'''-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(3'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-amino-3''-(3'''-hydroxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-N-(2-propenyl)amino-3''-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone; and 17-ethyl-1-hydroxy-12-[2'-(4''-(acetylamino-3''-4'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(2'''R-hydroxypropyl)amino-3''-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(2'''S-hydroxypropyl)amino-3''-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4''-(2'''R-hydroxypropyl)amino-3''-(4'''-methyl)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4''-(2'''S-hydroxypropyl)amino-3''-(4'''-methyl)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4''-(2'''R-hydroxypropyl)amino-3''-(4'''-methoxy)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4''-(2'''S-hydroxypropyl)amino-3''-(4'''-methoxy)phenyloxycyclohexyl)-1'-methylvinyl]-23,25-dimethoxy-13,19,21,27-tetra-methyl-11,28-dioxa-4-azatricyclo[22.3.1.0⁴,⁹]-octacos-18-ene-2,3,10,16-tetraone;

17-ethyl-1-hydroxy-12-[2'-(4''-(2'''R-hydroxypropyl)amino-3''-allyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-(2'''S-hydroxypropyl)amino-3''-allyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-dimethylamino-3''-(3'''-methoxy)phenyloxycyclohexyl)-1'-methylvinyl]23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-azido-3''-(4'''-dimethylamino)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(4'''-dimethylamino)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(4'''-methyl)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(4'''-hydroxymethyl)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(4'''-methoxy)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(3'''-methoxy)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(4'''-hydroxy)phenyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1-hydroxy-12-[2'-(4''-amino-3''-(4'''-formyl)phenyloxycyclohexyl)-1'-methylvinyl]-23,25-dimethoxy-13,19,21,27-tetramethyl-11,28-dioxa-4-azatricyclo[22.3.1.0^{4,9}]-octacos-18-ene-2,3,10,16-tetraone;
and pharmaceutically acceptable salts thereof.
5. The compound of claim 4 which is:
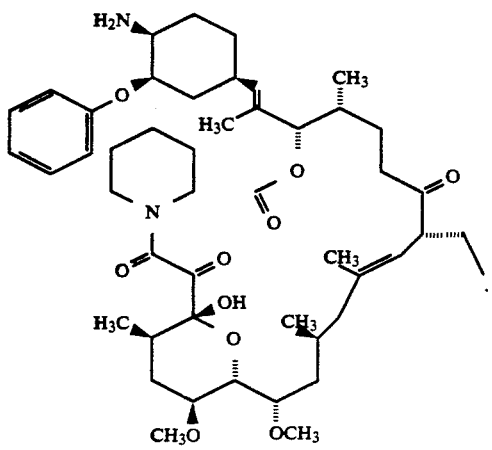
6. The compound of claim 4 which is:
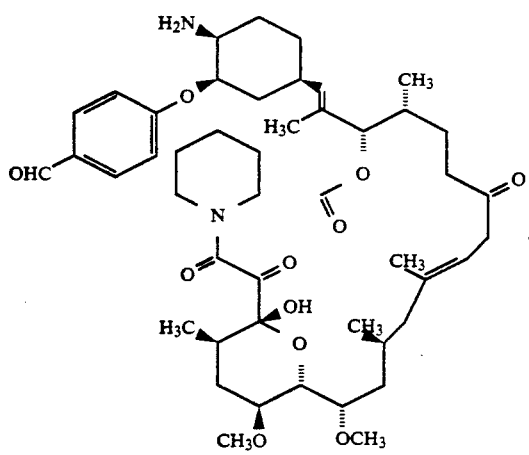
7. The compound of claim 4 which is:
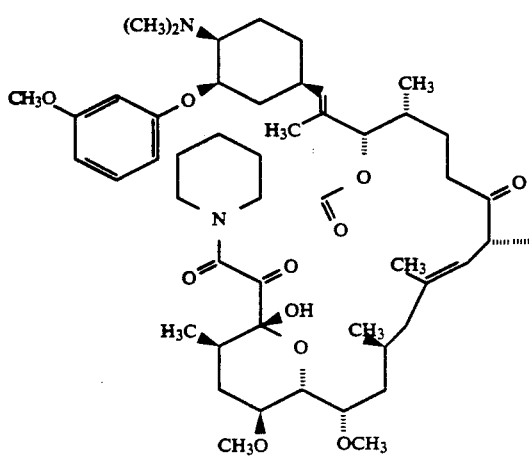
8. The compound of claim 4 which is:
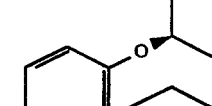
9. The compound of claim 4 which is:
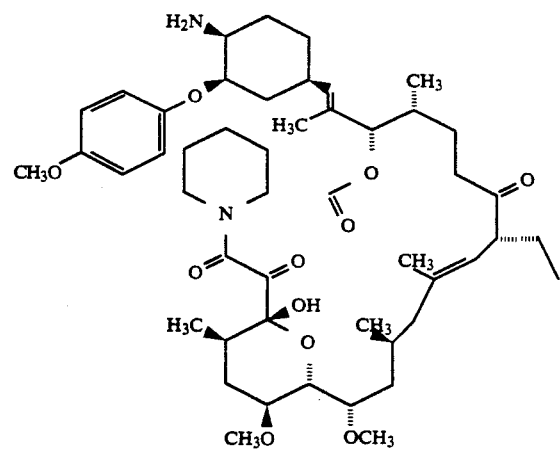
10. The compound of claim 4 which is:
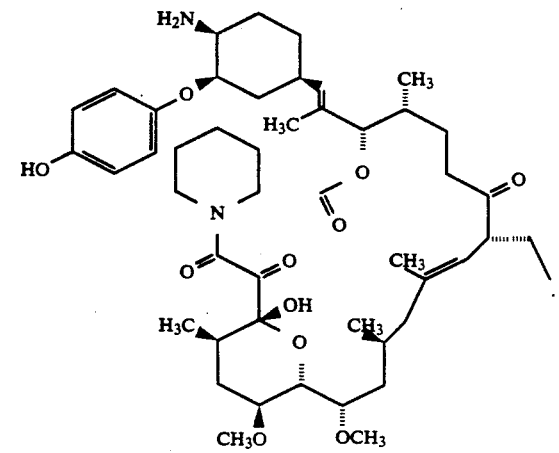
11. The compound of claim 4 which is:

12. The compound of claim 4 which is:
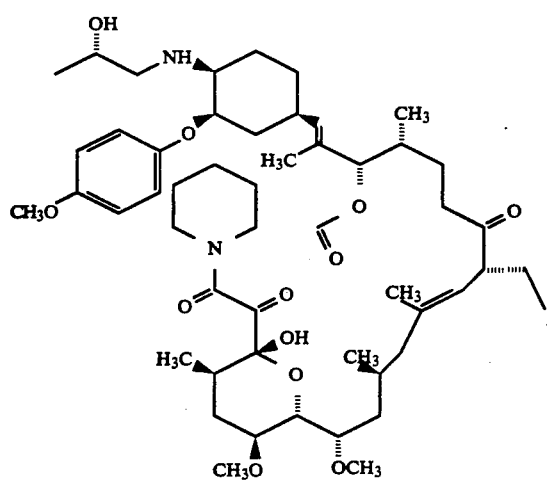
13. The compound of claim 4 which is:
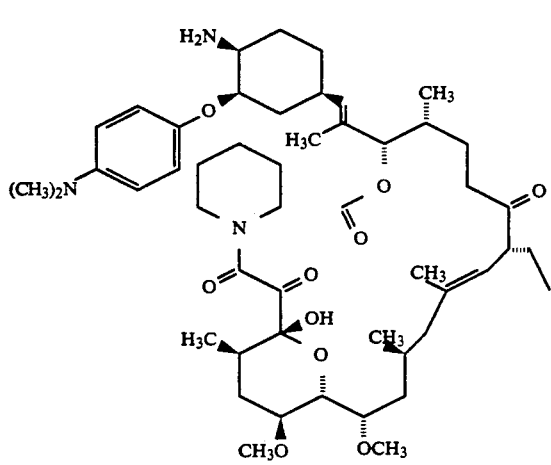
14. The compound of claim 4 which is:
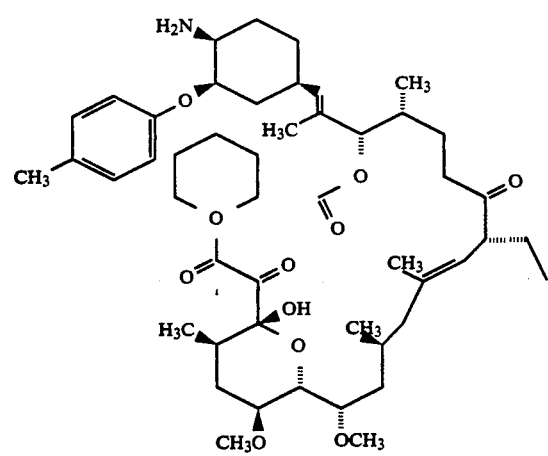
15. The compound of claim 4 which is:
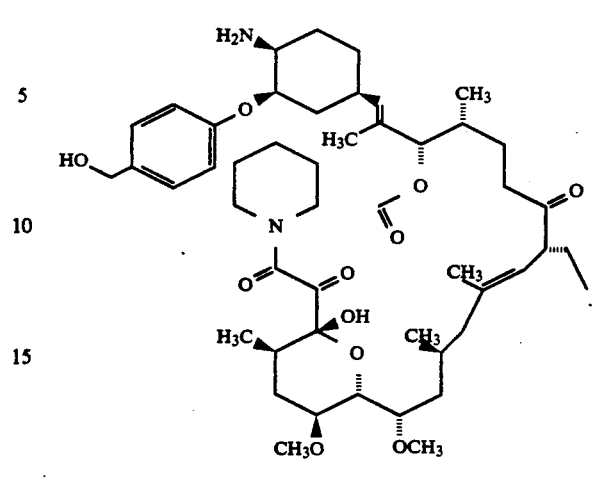
16. The compound of claim 4 which is:
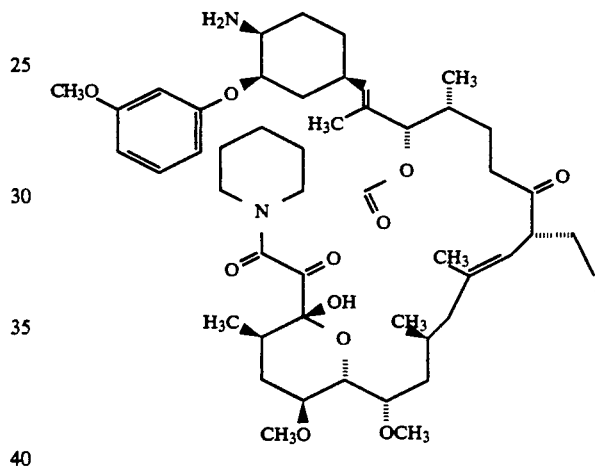
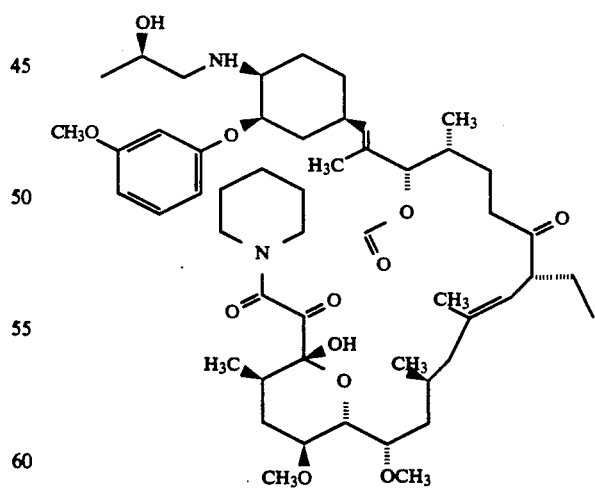
* * * * *